(12) United States Patent
Mitsuhashi et al.

(10) Patent No.: US 7,129,067 B2
(45) Date of Patent: Oct. 31, 2006

(54) METHOD FOR PRODUCING LACTONE

(75) Inventors: Katsuhisa Mitsuhashi, Kanagawa (JP); Makoto Iimori, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/519,212

(22) PCT Filed: Jun. 27, 2003

(86) PCT No.: PCT/JP03/08217

§ 371 (c)(1), (2), (4) Date: Dec. 27, 2004

(87) PCT Pub. No.: WO2004/003213

PCT Pub. Date: Jan. 8, 2004

(65) Prior Publication Data

US 2005/0130278 A1 Jun. 16, 2005

(30) Foreign Application Priority Data

Jun. 28, 2002 (JP) .............................. 2002-190616

(51) Int. Cl.
*C12P 17/02* (2006.01)
*C12P 17/06* (2006.01)
*C12P 17/04* (2006.01)
*C12N 1/16* (2006.01)

(52) U.S. Cl. .................. 435/123; 435/125; 435/126; 435/254.22; 435/255.4

(58) Field of Classification Search ................ 435/125, 435/126, 254.22, 255.4, 123
See application file for complete search history.

(56) References Cited

U.S. PATENT DOCUMENTS

| | | | |
|---|---|---|---|
| 4,560,656 A | 12/1985 | Farbood et al. | |
| 4,950,607 A | 8/1990 | Cardillo et al. | |
| 5,128,261 A | 7/1992 | Maria de Laat et al. | |
| 5,219,742 A | 6/1993 | Cheetham et al. | |
| 5,420,306 A | 5/1995 | Noyori et al. | |
| 5,527,693 A | 6/1996 | Cardillo et al. | |
| 5,789,212 A | 8/1998 | Boog et al. | |
| 5,792,871 A * | 8/1998 | Chartrain et al. ........... | 546/335 |
| 5,846,791 A * | 12/1998 | Chartrain et al. ........... | 435/122 |
| 6,451,565 B1 | 9/2002 | Rabenhorst et al. | |

FOREIGN PATENT DOCUMENTS

| | | |
|---|---|---|
| EP | 258993 A2 | 3/1988 |
| EP | 356291 A1 | 2/1990 |
| EP | 371568 A1 | 6/1990 |
| EP | 0 997 533 A1 | 5/2000 |
| JP | 59-82090 | 5/1984 |
| JP | 60-66991 A | 4/1985 |
| JP | 61-195693 A | 8/1986 |
| JP | 63-56295 | 3/1988 |
| JP | 2-174685 | 7/1990 |
| JP | 03-117494 | 5/1991 |
| JP | 3-155792 | 7/1991 |
| JP | 4-108782 | 4/1992 |
| JP | 4-108782 A | 4/1992 |
| JP | 06-225781 | 8/1994 |
| JP | 2002-528089 | 9/2002 |
| WO | WO 83/01072 A1 | 3/1983 |

OTHER PUBLICATIONS

Tahara et al., "γ-Decalactone-One of Constituents of Volatiles in Cultured Broth of *Sporobolomyces odorus*," Agr. Biol. Chem., vol. 36, No. 13, p. 2585-2587 (1972).
Sarris et al., "Production of Odoriferous γ Lactones by *Fusarium poae*," Agric. Biol. Chem., vol. 49, No. 11, pp. 3227-3230 (1985).
Maume et al., "The Production of γ-Decalactone by Fermentation of Castor Oil," Biocatalysis, vol. 5, pp. 79-97 (1991).
Okui et al., "Metabolism of Hydroxy Fatty Acids," The Journal of Biochemistry, vol. 54, No. 6, pp. 536-540 (1963).
Bernreuther et al., "Determination of the Enantiomeric Composition of γ-lactones in Complex Natural Matrices Using Multidimensional Capillary Gas Chromatography," Journal of Chromatography, vol. 481, pp. 363-367 (1989).
Jourdain et al., "Aroma Components Production by Immobilized Microbial Cells," Topics in Flavour Research, Proceedings of the International Conference, Freising—Weihenstephan, Apr. 1-2, 1985, pp. 427-441, H. Eichhom, Germany.

* cited by examiner

*Primary Examiner*—Herbert J. Lilling
(74) *Attorney, Agent, or Firm*—Finnegan, Henderson, Farabow, Garrett, & Dunner, LLP

(57) ABSTRACT

This invention relates to a method for producing a lactone comprising culturing *Candida sorbophila* in a medium containing at least one selected from the group consisting of a hydroxy fatty acid, a hydroxy fatty acid derivative, and a hydrolysate of a hydroxy fatty acid derivative and recovering the produced lactone from the medium. This invention also relates to a method for producing a lactone comprising culturing *Candida sorbophila* in a medium containing at least one selected from the group consisting of a hydroxy fatty acid, a hydroxy fatty acid derivative, and a hydrolysate of a hydroxy fatty acid derivative and lactonizing the lactone precursor hydroxy fatty acid produced in the medium.

20 Claims, No Drawings

METHOD FOR PRODUCING LACTONE

TECHNICAL FIELD

The present invention relates to a method for producing a lactone, which is useful for flavor and fragrance substances, pharmaceutical intermediates, and the like, with the use of microorganisms.

BACKGROUND ART

Aromatic substances are roughly classified into two categories: that is, chemically synthesized (so-called "synthetic aromatics"); and non-chemically synthesized (so-called "natural aromatics"), depending on the starting material thereof or the method for producing the same. Recently, consumers tend to prefer "natural products" over "synthetic products." However, natural substances contain only very small amounts of, for example, optically active substances of γ-decalactone (R-γ-decalactone or S-γ-decalactone) and δ-decalactone, which are important ingredients of natural food flavor. Thus, processes such as extraction of such optically active substances with high optical purity or isolation thereof via other means are disadvantageous from technical and economical viewpoints. As a result, large quantities of synthetic products are generally supplied at low prices at present. In contrast, the scale of manufacturing natural products is small, and such natural products are often expensive.

Development of a method for supplying large quantities of the aforementioned natural aromatics at prices as low as those of currently used synthetic aromatics has been awaited. Among the methods for supplying large quantities of natural aromatics that have been proposed a microorganism-based fermentation technique has drawn attention. In this technique, natural R-γ-decalactone is produced from natural materials or degradation products thereof via biological or physical techniques without any chemical techniques.

For example, JP Patent Publication (Kokai) No. 59-82090 A (1984) discloses a microorganism-based method for producing γ-decalactone from castor oil or a hydrolysate thereof. In this method, microorganisms such as *Aspergillus oryzae, Candida rugosa, Geotrichum klebannii,* and *Yarrowia lipolytica* are used to produce γ-hydroxydecanoic acid, and the resultant is acidified with the addition of hydrochloric acid or the like, followed by heating for lactonization, and thus γ-decalactone is produced. JP Patent Publication (Kokai) No.63-56295 A (1988) and the report by K. A. Maume et al. (Biocatalysis, vol. 5, 79–97, 1991) disclose a method for producing γ-decalactone wherein γ-hydroxydecanoic acid is produced from ricinoleic acid sources using *Sporobolomyces odorus* or *Rhodotorula glutinis*, and the resultant is also lactonized. JP Patent Publication No. 2-174685 A (1990) discloses a method for producing γ-decalactone from castor oil or ricinoleic acid via production of γ-hydroxydecanoic acid with the use of microorganisms such as *Aspergillus niger*. JP Patent Publication No. 3-117494 A (1991) discloses the same technique with the use of microorganisms such as *Saccharomyces cerevisiae*. Prior to the disclosure of these techniques, S. Okui et al. reported the presence of γ-hydroxydecanoic acid and γ-decalactone as intermediates during the process for oxidizing and degrading ricinoleic acid with the use of several cell strains of the genus *Candida* (J. Biochem., vol. 54, No. 6, 536–540, 1963). Also, EP 997533 discloses a method for producing γ-decalactone from castor oil at 12 g per liter using *Yarrowia lipolytica*. This method for production, however, is extremely disadvantageous from the viewpoint of production efficiency due to the necessity of the use of an emulsifier or pH adjuster during the culture and a small amount of a starting material, i.e., castor oil, to be added to the culture system, which is as low as 0.0247 kg/L. Further, the microorganisms disclosed in such publications and the like, which are of species different from those of the microorganisms used in the present invention, are not always suitable for practical use because of the difficulty of separation of cell strains from culture products and insufficient amounts of production from an economical viewpoint.

Alternatively, a method for producing γ-decalactone from a sugar substrate with the aid of *Sporobolomyces odorus* (S. Taqhara et al., Agric. Biol. Chem., vol. 36, No. 13, 2585–2587, 1972; N. Jourdain et al., "Top. Flavour Res., Proc. Int. Conf," H. Eichhorn, 427–441, 1985) or *Fusarium poae* (J. Sarris et al., Agric. Biol. chem., vol. 49, No. 11, 3227–3230, 1985), which is an example of methods in which a component other than castor oil or a hydrolysate thereof is employed as a carbon source, has been reported. However, these techniques are not suitable for industrial-scale production since only a very small amount of γ-decalactone is produced.

Accordingly, development of a method for effectively producing γ-hydroxydecanoic acid and γ-decalactone that does not require the use of an emulsifier or pH adjuster and that allows the addition of a highly concentrated starting material, i.e., castor oil and/or a hydrolysate thereof, has been awaited.

It is also reported that the abundance of R-γ-decalactone enantiomer in naturally occurring γ-decalactone is excessive (A. Bernreuther et al., J. Chromatography, 481, 363, 1989). A method for producing a pure optically active form of such R-γ-decalactone via chemical synthesis is disclosed in JP Patent Publication No. 4-108782 A (1992).

R-γ-decalactone can also be produced by selectively separating R-γ-decalactone from racemic mixtures as extracted from natural substances by a technique known to a person skilled in the art. Because of the very small amount of R-γ-decalactone in natural substances and a physical difficulty in separating R-γ-decalactone from other volatile compounds, however, extraction thereof from natural substances is not cost-effective. In order to deal with increasing demands for natural compounds as mentioned above, development of a method for effectively producing natural R-γ-decalactone using techniques different from the chemical synthesis thereof or the separation thereof from racemic mixtures, has been awaited.

A method for producing δ-decalactone using microorganisms, which makes use of the reducing ability of fungi, particularly that of yeast, has been proposed. For example, JP Patent Publication No. 3-155792 A (1991) discloses a method for producing 5-decanolide from naturally occurring 2-decen-1,5-olide with the utilization of the reducing ability of *Saccharomyces cerevisiae*. JP Patent Publication No. 6-225781 A (1994) reports a method for producing δ-decanolide, δ-dodecanolide, or a mixture thereof from a substrate material containing a corresponding unsaturated lactone, i.e., δ-decen-2-olide, δ-dodecen-2-olide, or a mixture thereof, via biohydrogenation with the use of yeast such as *Saccharomyces delbrueckii*. However, a technique of chemical conversion utilizing the reducing ability of yeast is still problematic in terms of, for example, the difficulty in acting on high concentrations of the substrate and the necessity of a long period of time to obtain the substance of interest.

DISCLOSURE OF THE INVENTION

This application claims the priority of Japanese Patent Application No. 2002-190616, the disclosure of which is incorporated herein.

The present invention has been made in order to overcome the problems mentioned above. It is an object of the present invention to provide a method for effectively producing a natural lactone including an optically active lactone such as an optically active γ-decalactone and an optically active δ-decalactone, with the use of microorganisms.

In order to attain the above object, the present inventors have searched for microorganisms extensively from existing cell strains and in nature that can accumulate highly concentrated γ-hydroxydecanoic acid in a culture medium with castor oil and/or a hydrolysate thereof as a carbon source. As a result, they have found that use of *Candida sorbophila* enabled production and accumulation of γ-hydroxydecanoic acid and/or an optically active γ-decalactone in a culture medium with high efficiency while using no emulsifier or pH adjuster and adding at least one starting material selected from the group consisting of castor oil, a castor oil hydrolysate, ricinoleic acid, and lesquerolic acid at high concentration. Further, they have also found that optically active γ-decalactone could be easily produced by heating the obtained γ-hydroxydecanoic acid under acidic conditions. The thus produced optically active γ-decalactone was recovered with very high productivity. Furthermore, they have also found that the aforementioned *Candida sorbophila* enabled the production of a variety of optically active lactones by employing a variety of hydroxy fatty acids as carbon sources.

The present invention has been completed based on such findings and is as described below.

(1) A method for producing a lactone comprising culturing *Candida sorbophila* in a medium containing at least one selected from the group consisting of a hydroxy fatty acid, a hydroxy fatty acid derivative, and a hydrolysate of a hydroxy fatty acid derivative, and recovering the produced lactone from the medium.

(2) A method for producing a lactone comprising culturing *Candida sorbophila* in a medium containing at least one selected from the group consisting of a hydroxy fatty acid, a hydroxy fatty acid derivative, and a hydrolysate of a hydroxy fatty acid derivative and lactonizing a lactone precursor hydroxy fatty acid produced in the medium.

(3) The method according to (1) or (2), wherein the *Candida sorbophila* is at least one selected from the group consisting of the *Candida sorbophila* strain ATCC 74362, the *Candida sorbophila* strain ATCC 60130, the *Candida sorbophila* strain IFO 1583, and the *Candida sorbophila* strain FC 58 deposited under the accession number FERM BP-8388.

(4) The method according to (1) or (2), wherein the lactone is represented by the general formula (1):

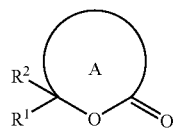

wherein ring A represents a lactone ring; $R^1$ represents a hydrogen atom, a hydrocarbon group, a substituted hydrocarbon group, a heterocyclic group, or a substituted heterocyclic group; and $R^2$ represents a hydrogen atom a hydrocarbon group or a substituted hydrocarbon group; in which ring A and $R^2$ may be bonded to form a ring.

(5) The method according to (1) or (2), wherein the lactone is an optically active lactone.

(6) The method according to (1) or (2), wherein the hydroxy fatty acid is represented by the general formula (2):

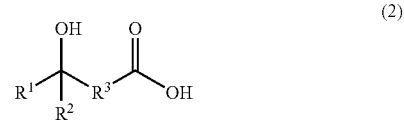

wherein $R^1$ represents a hydrogen atom, a hydrocarbon group, a substituted hydrocarbon group, a heterocyclic group, or a substituted heterocyclic group; $R^2$ represents a hydrogen atom, a hydrocarbon group, or a substituted hydrocarbon group; and $R^3$ represents an optionally substituted divalent hydrocarbon group having a 4 or more-carbon chain; in which $R^2$ and $R^3$ may be bonded to form a ring.

(7) The method according to (1) or (2), wherein the hydroxy fatty acid derivative is an alkyl ester of hydroxy fatty acid or a glyceride of hydroxy fatty acid.

(8) The method according to (7), wherein the alkyl ester of hydroxy fatty acid is represented by the general formula (3):

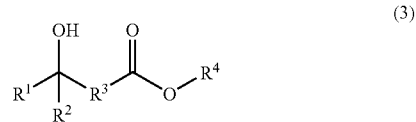

wherein $R^1$ represents a hydrogen atom, a hydrocarbon group, a substituted hydrocarbon group, a heterocyclic group, or a substituted heterocyclic group; $R^2$ represents a hydrogen atom, a hydrocarbon group, or a substituted hydrocarbon group; $R^3$ represents an optionally substituted divalent hydrocarbon group having a 4 or more-carbon chain; and $R^4$ represents an alkyl group; in which $R^2$ and $R^3$ may be bonded lo form a ring.

(9) The method according to (7), wherein the glyceride of hydroxy fatty acid is represented by the general formula (4):

wherein $R^6$ to $R^8$ each independently represents a hydrogen atom or a group represented by the general formula (6):

wherein $R^1$ represents a hydrogen atom, a hydrocarbon group, a substituted hydrocarbon group, a heterocyclic group, or a substituted heterocyclic group; $R^2$ represents a hydrogen atom, a hydrocarbon group, or a substituted hydrocarbon group; $R^3$ represents an optionally substituted divalent hydrocarbon group having a 4 or more-carbon chain; and $R^4$ represents an alkyl group; in which $R^2$ and $R^3$ may be bonded to form a ring, provided that at least one of $R^6$ to $R^8$ is a group represented by the above general formula (6).

(10) The method according to (1) or (2), wherein *Candida sorbophila* is cultured in a medium containing at least one selected from the group consisting of castor oil, a castor oil hydrolysate, ricinoleic acid, 11-hydroxypalmitic acid, lesquerolic acid, 10-hydroxystearic acid, 10-hydroxypalmitic acid, and ethyl 11-hydroxypalmitate.

(11) The method according to (2), wherein the lactone precursor hydroxy fatty acid is a hydroxy fatty acid of 4 or more carbon atoms having a hydroxy group at position 4 or 5 thereof.

(12) The method according to (1) or (2), wherein the lactone is any one selected from the group consisting of γ-decalactone, γ-valerolactone, γ-hexalactone, γ-heptalactone, γ-octalactone, γ-nonalactone, γ-undecalactone, γ-dodecalactone, γ-tridecalactone, γ-tetradecalactone, δ-decalactone, δ-hexalactone, δ-heptalactone, δ-octalactone, δ-nonalactone, δ-undecalactone, δ-dodecalactone, δ-tridecalactone, and δ-tetradecalactone.

(13) A method for producing a lactone precursor hydroxy fatty acid comprising culturing *Candida sorbophila* in a medium containing at least one selected from the group consisting of a hydroxy fatty acid, a hydroxy fatty acid derivative, and a hydrolysate of a hydroxy fatty acid derivative.

(14) A method for producing γ-decalactone comprising culturing *Candida sorbophila* in a medium containing at least one selected from the group consisting of castor oil, a castor oil hydrolysate, ricinoleic acid, and lesquerolic acid, and recovering the produced γ-decalactone from the medium.

(15) A method for producing γ-decalactone comprising culturing *Candida sorbophila* in a medium containing at least one selected from the group consisting of castor oil, a castor oil hydrolysate, ricinoleic acid, and lesquerolic acid, and lactonizing γ-hydroxydecanoic acid produced in the medium.

(16) The method according to (14) or (15), wherein γ-decalactone is an optically active γ-decalactone.

(17) The method according to (14) or (15), wherein at least one selected from the group consisting of castor oil, a castor oil hydrolysate, ricinoleic acid, and lesquerolic acid is castor oil and/or a castor oil hydrolysate.

(18) A method for producing δ-decalactone comprising culturing *Candida sorbophila* in a medium containing 11-hydroxypalmitic acid and/or ethyl 11-hydroxypalmitate and recovering the produced δ-decalactone from the medium.

(19) A method for producing δ-decalactone comprising culturing *Candida sorbophila* in a medium containing 11-hydroxypalmitic acid and/or ethyl 11-hydroxypalmitate and lactonizing δ-hydroxydecanoic acid produced in the medium.

(20) The method according to (18) or (19), wherein δ-decalactone is an optically active δ-decalactone.

(21) The method according to (14), (15), (18), or (19), wherein the *Candida sorbophila* is at least one selected from the group consisting of the *Candida sorbophila* strain ATCC 74362, the *Candida sorbophila* strain ATCC 60130, the *Candida sorbophila* strain IFO 1583, and the *Candida sorbophila* strain FC 58 deposited under the accession number FERM BP-8388.

(22) Use of *Candida sorbophila* for producing a lactone.

(23) A *Candida sorbophila* strain FERM BP-8388.

The production method of a lactone according to the present invention is carried out by culturing *Candida sorbophila* in a medium containing at least one selected from the group consisting of a hydroxy fatty acid, a hydroxy fatty acid derivative, and a hydrolysate of a hydroxy fatty acid derivative to produce a lactone and then recovering the lactone from the medium.

The production method of a lactone according to the present invention is also carried out by culturing *Candida sorbophila* in a medium containing at least one selected from the group consisting of a hydroxy fatty acid, a hydroxy fatty acid derivative, and a hydrolysate of a hydroxy fatty acid derivative to produce a lactone precursor hydroxy fatty acid and then lactonizing the lactone precursor hydroxy fatty acid.

Hereafter, the method for producing a lactone according to the present invention is described in detail.

(1) *Candida sorbophila*

Specific examples of *Candida sorbophila* used in the present invention include, but are not limited to, the *Candida sorbophila* strain FC 58, the *Candida sorbophila* strain ATCC 74362, the *Candida sorbophila* strain ATCC 60130, and the *Candida sorbophila* strain IFO 1583. The *Candida sorbophila* strain FC 58 was deposited at the International Patent Organism Depository of the National Institute of Advanced Industrial Science and Technology (Tsukuba Central 6, 1-1-1 Higashi, Tsukuba, Ibaraki, Japan) as of Jun. 10, 2002 under the accession number: FERM BP-8388 (the original deposit). A request for transfer of the deposition from the original to the international deposition under the Budapest Treaty was accepted as of May 28, 2003.

The aforementioned *Candida sorbophila* strain FC 58 was separated from common soil in Kanagawa prefecture, Japan, in accordance with a conventional technique, the mycological properties thereof were identified, and the identified properties were studied in accordance with the taxonomic textbooks (Kurtzman, C. P. et al., "The Yeasts, A Taxonomic Study" 4th edition, 1998, Elsevier Science B. V.; and Barnett, J. A. et al., "Yeasts: Characteristics and identification" 3rd ed). As a result, the *Candida sorbophila* strain FC 58 was identified to be a microorganism of the genus *Candida sorbophila*. Thus, this microorganism separated from nature was designated as the *Candida sorbophila* strain FC 58 (hereafter abbreviated as the "FC 58 strain").

The mycological properties of the FC 58 strain that can be preferably used in the present invention are as follows.

(1) Growth in YM liquid medium: the form primarily changes from spherical to oval after the strain has been cultured at 24° C. to 27° C. for 24 hours.

(2) Growth in YM agar medium: the color of the strain becomes between white and cream and the strain is moistened after it has been cultured at 24° C. to 27° C. for 2 to 3 days.

(3) Form: spherical to oval, proliferated by multipolar budding, formation of pseudomycelium and formation of ascospore when it is cultured in medium of Adams, Gorodokowa, malt, YM, V-8, or potato dextrose are not observed.

(4) Optimal growth conditions: at 24° C. to 27° C., pH 5.5 to 6.0.

(5) Maximal temperature for growth: at 35° C. to 37° C.

(6) Vitamin requirement: it cannot grow in a vitamin-deficient medium Biotin, pyridoxine, or thiamine is required.

(7) Fermentation: glucose (−), galactose (−), sucrose (−), maltose (−), lactose (−), raffinose (−), trehalose (−).

(8) Assimilability: galactose (+), sorbose (+), sucrose (−) maltose (−), trehalose (−), lactose (−), raffinose (−), cellobiose (−), melibiose (−), melezitose (−), starch (−), D-xylose (−), L-arabinose (−), D-ribose. (−), D-rhamnose (−), D-glucosamine (−), N-acetyl-D-glucosamine (−), glycerol (weak), erythritol (−), ribitol (−), D-mannitol (+), lactate (weak), citrate (−), inositol (−)

The aforementioned "ATCC" and "IFO" are abbreviations of "American Type Culture Collection" and "Institution for Fermentation, Osaka, Japan," respectively. A numerical value provided with "ATCC" or "IFO" represents the catalog number of each strain. The aforementioned *Candida sorbophila* represented by the numerical value following "ATCC" or "IFO" can be obtained from respective organizations based on those catalog numbers.

When the *Candida sorbophila* used in the present invention is cultured in a medium containing a hydroxy fatty acid, a hydroxy fatty acid derivative, and/or a hydrolysate of a hydroxy fatty acid derivative, it can produce a lactone precursor hydroxy fatty acid by β-oxidation, and then may produce a lactone by lactonizing the generated lactone precursor hydroxy fatty acid, resulting in accumulation of them in the medium. When the *Candida sorbophila* used in the present invention is cultured in a medium containing a hydroxy fatty acid derivative under adequate culture conditions, this strain hydrolyzes the hydroxy fatty acid derivative and then β-oxidizes the hydrolysate to produce a lactone precursor hydroxy fatty acid. The product is then accumulated in the medium. In such a case, lactonization of the lactone precursor hydroxy fatty acid that is produced and accumulated in the medium can result in the generation of a desired lactone.

When the *Candida sorbophila* used in the present invention is cultured in a medium containing, for example, castor oil, it can hydrolyze the castor oil. Further, during the culture, γ-hydroxydecanoic acid and/or γ-decalactone can be produced and accumulated in the medium by β-oxidation of a hydrolysate of such castor oil.

(2) Medium for Producing a Lactone

In the present invention, a medium that contains at least one member, as a carbon source, selected from the group consisting of a hydroxy fatty acid, a hydroxy fatty acid derivative, and a hydrolysate of a hydroxy fatty acid derivative and in which *Candida sorbophila* can grow, is used in the present method for producing a lactone.

The hydroxy fatty acid or hydrolysate of a hydroxy fatty acid derivative used in the present invention is not particularly limited as long as it can be β-oxidized by *Candida sorbophila*, thereby producing the lactone precursor hydroxy fatty acid. The hydroxy fatty acid derivative used in the present invention is not particularly limited as long as it is hydrolyzed by *Candida sorbophila* and the lactone precursor hydroxy fatty acid can be produced from the resulting hydrolysate via β-oxidation.

The hydroxy fatty acid, which has 6 or more, preferably 6 to 25, and more preferably 6 to 20 carbon atoms, and has a hydroxy group in at least the 6-position, and preferably in the 6- to 20-positions from the carbon atom in the carboxy group, is preferably used in the present invention.

A specific example of a hydroxy fatty acid, for example, is represented by the general formula (2):

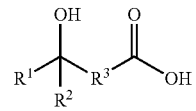

(2)

wherein $R^1$ represents a hydrogen atom, a hydrocarbon group, a substituted hydrocarbon group, a heterocyclic group, or a substituted heterocyclic group; $R^2$ represents a hydrogen atom, a hydrocarbon group, or a substituted hydrocarbon group; $R^3$ represents an optionally substituted divalent hydrocarbon group having a 4 or more-carbon chain; in which either $R^1$ and $R^2$ or $R^2$ and $R^3$ may be bonded to form a ring.

These groups in the general formula (2) are described below.

Examples of the hydrocarbon group, for example, include alkyl, alkyl having an unsaturated bond, aryl, aralkyl and the like.

Alkyl may be linear, branched, or cyclic. For example, alkyl has at least one preferably 1 to 20, more preferably 1 to 15, and further preferably 1 to 10 carbon atoms. Specific examples thereof include methyl, ethyl, n-propyl, 2-propyl, n-butyl, 2-butyl, isobutyl, tert-butyl, n-pentyl, 2-pentyl, tert-pentyl, 2-methylbutyl, 3-methylbutyl, 2,2-dimethylpropyl, n-hexyl, 2-hexyl, 3-hexyl, tert-hexyl, 2-methylpentyl, 3-methylpentyl, 4-methylpentyl, 2-methylpentan-3-yl, n-heptyl, n-octyl, n-nonyl, n-decyl, cyclopropyl, cyclobutyl, cyclopentyl, and cyclohexyl.

The alkyl having an unsaturated bond includes alkyl having at least one unsaturated bond such as a double bond and the like in its chain. Specific examples thereof include alkenyl, alkadienyl, alkatrienyl and the like.

Alkenyl has one double bond in the chain of the aforementioned alkyl. For example, it may be linear, branched, or cyclic, and it may have at least 2, preferably 2 to 20, more preferably 2 to 15, and further preferably 2 to 10 carbon atoms. Specific examples thereof include ethenyl, propenyl, butenyl, pentenyl, hexenyl, octenyl, nonanyl, decenyl and the like.

Alkadienyl has two double bonds in the chain of the aforementioned alkyl. For example, it may be linear, branched, or cyclic, and it may have at least 4, preferably 4 to 20, more preferably 4 to 15, and further preferably 4 to 10 carbon atoms. Specific examples thereof include 1,3-butadienyl, 2,4-butadienyl, 2,3-dimethyl-1,3-butadienyl and the like.

The aryl includes one that has 6 to 14 carbon atoms. Specific examples thereof include phenyl, naphthyl, anthryl, biphenyl and the like.

The aralkyl includes a group derived from the aforementioned alkyl by substitution of at least one hydrogen atom with the aforementioned aryl. For example, aralkyl preferably has 7 to 12 carbon atoms. Specific examples thereof include benzyl, 2-phenylethyl, 1-phenylpropyl, 3-naphthylpropyl and the like.

Examples of the heterocyclic group include an aliphatic heterocyclic group and an aromatic heterocyclic group.

The aliphatic heterocyclic group includes, for example, a 5- to 8-membered and preferably a 5- or 6-membered monocyclic, polycyclic, or fused-ring aliphatic heterocyclic group, which has 2 to 14 carbon atoms and contains as heteroatoms at least one and preferably 1 to 3 heteroatoms, such as nitrogen, oxygen, and sulfur atoms. Specific examples of the aliphatic heterocyclic group include, for example, pyrrolidyl-2-one, piperidino, piperazinyl, morpholino, tetrahydrofuryl, tetrahydropyranyl and the like.

The aromatic heterocyclic group, for example, includes a 5- to 8-membered and preferably a 5- or 6-membered monocyclic, polycyclic, or fused-ring heteroaryl, which has 2 to 15 carbon atoms, and contains as heteroatoms at least one and preferably 1 to 3 heteroatoms, such as a nitrogen, oxygen and sulfur atom. Specific examples thereof include furyl, thienyl, pyridyl, pyrimidyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthylidyl, cinnolyl, benzimidazolyl, benzoxazolyl, benzothiazolyl and the like.

The substituted hydrocarbon group includes substituted alkyl, substituted alkyl having an unsaturated bond, substituted aryl, and substituted aralkyl, wherein at least one hydrogen atom in the aforementioned hydrocarbon group has been substituted with a substituent.

The aforementioned substituent includes hydrocarbon group, substituted hydrocarbon, heterocyclic group, heterocyclic group, alkoxy, aryloxy, aralkyloxy, alkoxycarbonyl, aryloxycarbonyl, aralkyloxycarbonyl, acyl, acyloxy, alkylthio, aralkylthio, arylthio, halogen, alkylenedioxy, amino, substituted amino, hydrazino, cyano, nitro, hydroxy, hydroxy substituted with a protecting group, carboxy, sulfonylamino, sulfo, amide phosphate, substituted silyl and the like.

These groups represented by $R^1$ are preferably alkyl or alkyl having an unsaturated bond among them.

The divalent hydrocarbon group, which may have a substituent and contains a 4 or more-carbon chain, includes a divalent hydrocarbon group having a 4 or more-carbon chain and a divalent substituted hydrocarbon group having a 4 or more-carbon chain. The divalent hydrocarbon group having a 4 or more carbon chain includes alkylene, alkylene having an unsaturated bond, and a divalent aromatic group, which have an at least 4-carbon chain.

Alkylene having a 4 or more-carbon chain includes a linear, branched, or cyclic alkylene having an at least 4-, preferably 4 to 20-, and more preferably 4 to 15-carbon chain. Specific examples thereof include tetramethylene, pentamethylene, hexamethylene, heptamethylene, octamethylene, nonamethylene, decamethylene, and $—(CH_2)_m\text{-o-}C_6H_{10}—(CH_2)_n—$ and the like, wherein m and n are each independently 0 or a natural number, and $m+n \geqq 2$.

The alkylene that has a 4 or more-carbon chain and an unsaturated bond and the like includes an alkylene containing at least one unsaturated bond such as a double bond and the like in the 4 or more-carbon chain. The alkylene that has a 4 or more-carbon chain and an unsaturated bond may have an at least 4-, preferably 4 to 20-, and more preferably 4 to 15-carbon chain, and it may be linear, branched, or cyclic. Specific examples thereof include alkenylene such as butenylene, pentenylene, and hexenylene.

The divalent aromatic group having a 4 or more-carbon chain includes an at least 4-carbon chain-containing divalent aromatic group having an at least 4-, preferably 4 to 20-, and more preferably 4 to 15-carbon chain. A specific example thereof includes $—(CH_2)_p\text{-o-}C_6H_4—(CH_2)_q—$, wherein p and q are each independently 0 or a natural number, and $p+q \geqq 2$, and the like.

The divalent substituted hydrocarbon group containing a 4 or more-carbon chain includes a divalent substituted hydrocarbon group derived from a divalent hydrocarbon group containing a 4 or more-carbon chain by substituting at least 1 hydrogen atom thereof with the aforementioned substituent other than a hydroxy group.

When either $R^1$ and $R^2$ or $R^2$ and $R^3$ are bonded to form a ring, the ring formed includes an aliphatic ring, an aromatic ring and the like. The aliphatic ring includes a cyclobutane ring, a cyclopentane ring, a cyclohexane ring, a cyclohexene ring and the like. The aromatic ring includes a benzene ring.

Preferable examples of a hydroxy fatty acid include ricinoleic acid. 11-hydroxypalmitic acid; lesquerolic acid, 10-hydroxystearic acid and 10-hydroxypalmitic acid, and the lactone precursor hydroxy fatty acid represented by following formulae.

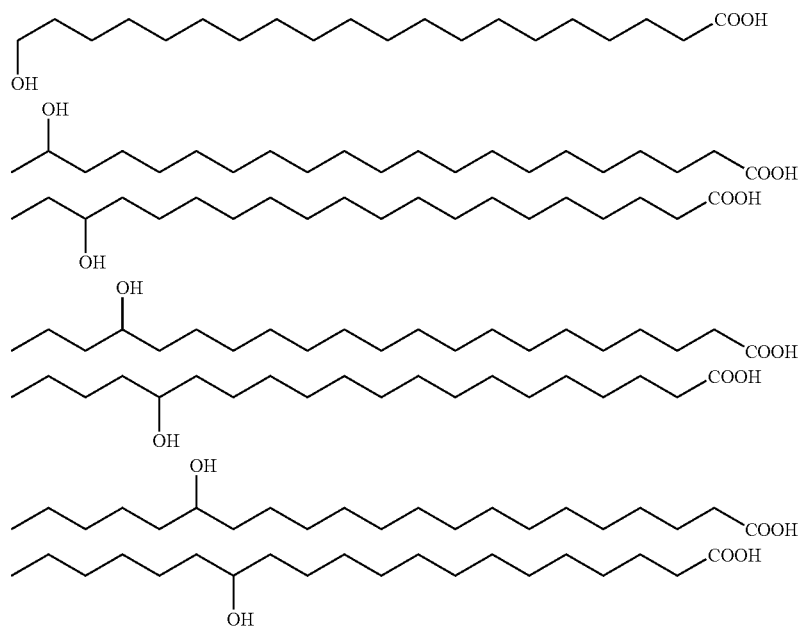

-continued
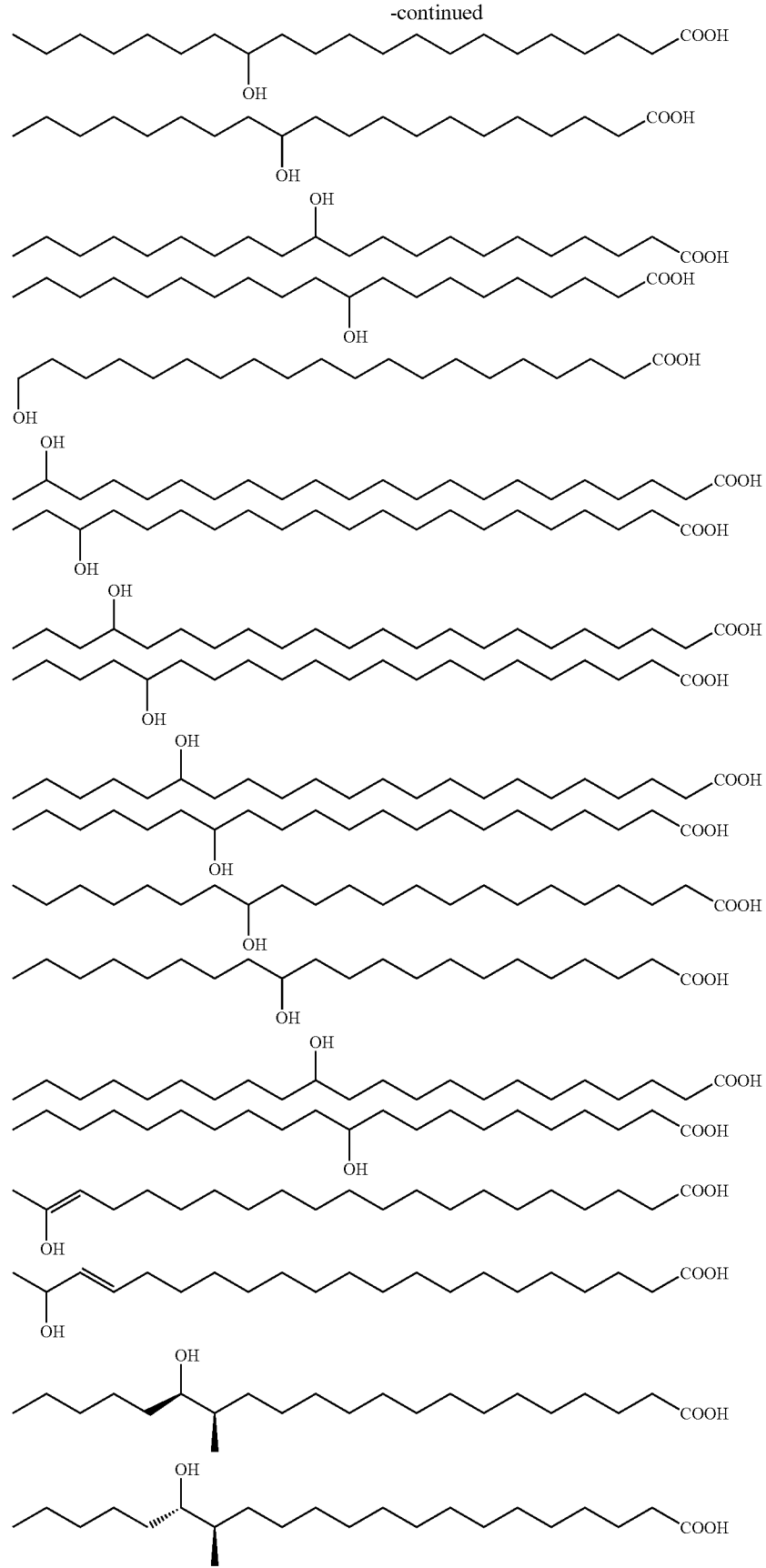

-continued
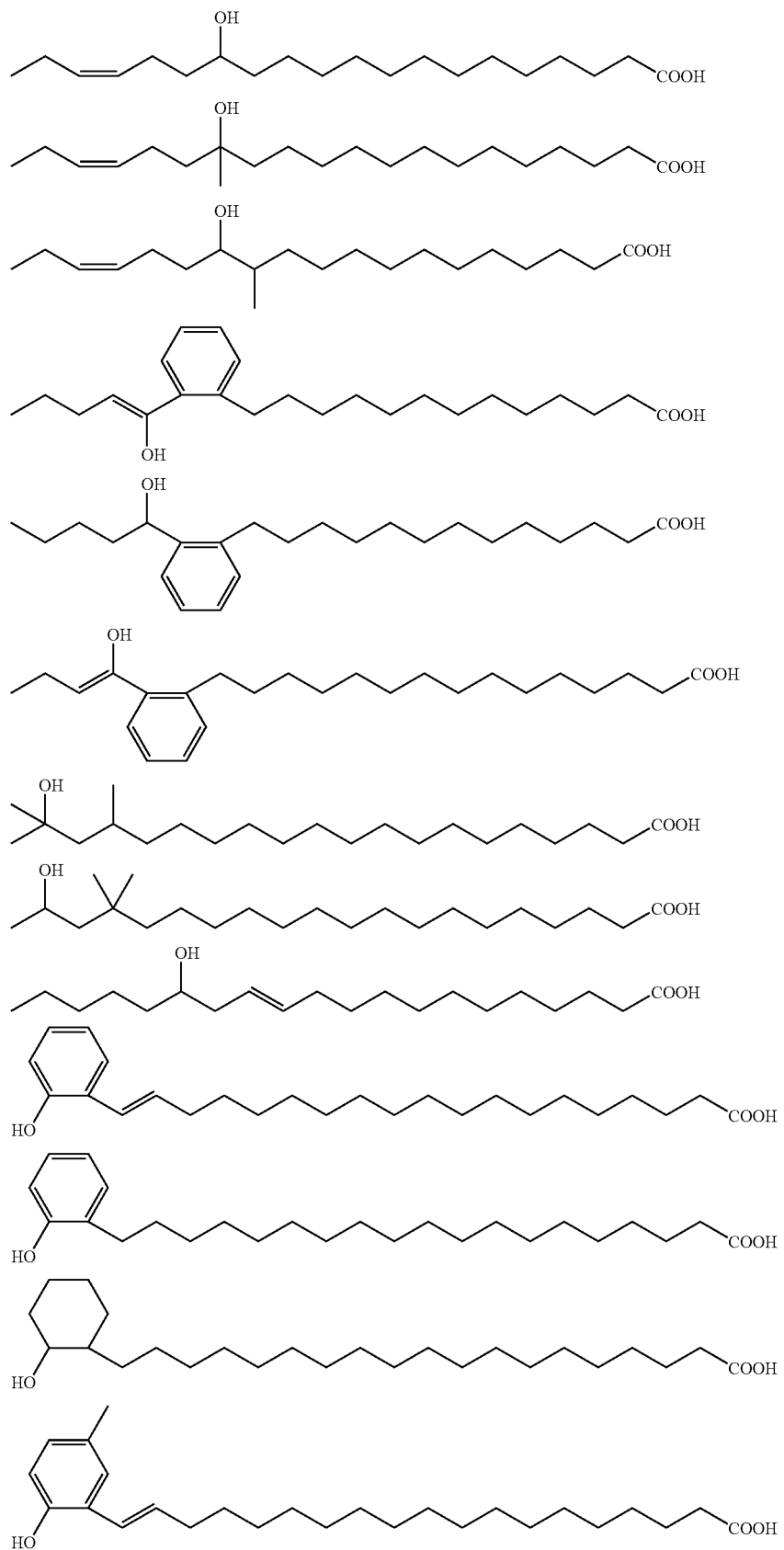

-continued

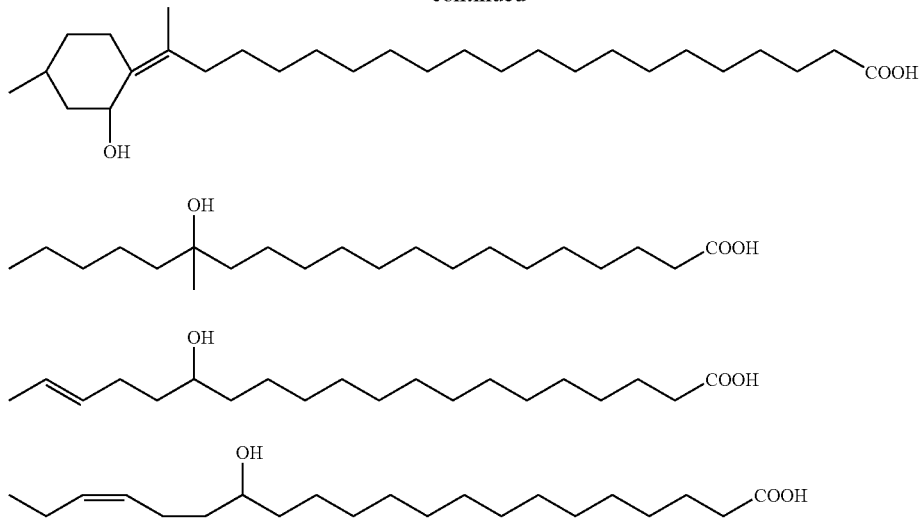

The aforementioned hydroxy fatty acid is preferably ricinoleic acid, 11-hydroxypalmitic acid, lesquerolic acid, 10-hydroxystearic acid, 10-hydroxypalmitic acid, or the like among them.

The hydroxy fatty acid derivative used in the present invention is preferably one derived from the aforementioned hydroxy fatty acid. Preferable examples of such hydroxy fatty acid derivative include an alkyl ester of hydroxy fatty acid, a glyceride of hydroxy fatty acid and the like.

A specific example of the alkyl ester of hydroxy fatty acid, for example, is represented by the general formula (3):

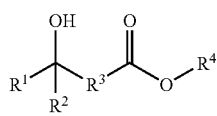

(3)

wherein $R^4$ represents alkyl and $R^1$ to $R^3$ are as defined above.

Alkyl represented by $R^4$ may be linear or branched. The alkyl includes an alkyl having at least one, preferably 1 to 10, more preferably 1 to 6, and further preferably 1 to 3 carbon atoms. Specific examples thereof include methyl, ethyl, n-propyl, 2-propyl and the like.

A preferable alkyl ester of hydroxy fatty acid in the present invention is one having 1 to 3 carbon atoms in its alkyl ester portion (for example, methyl ester, ethyl ester, and propyl ester etc.). Specific examples thereof include ethyl 11-hydroxypalmitate, ethyl ricinoleate, ethyl lesquerolate, ethyl 10-hydroxystearate, ethyl 10-hydroxypalmitate and the like.

The glyceride of hydroxy fatty acid includes a monoglyceride of hydroxy fatty acid, a diglyceride of hydroxy fatty acid, and a triglyceride of hydroxy fatty acid. A specific example thereof, for example, is represented by the general formula (4):

(4)

wherein $R^6$ to $R^8$ each independently represent a hydrogen atom or a group represented by the general formula (6):

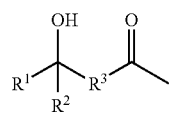

(6)

wherein $R^1$ to $R^3$ are as defined above, provided that at least one of $R^6$ to $R^8$ independently represents a group represented by the above general formula (6).

The glyceride of hydroxy fatty acid represented by the above-mentioned general formula (4) includes one obtained by condensation between a glycerin and the hydroxy fatty acid represented by the above-mentioned general formula (2).

A preferable example of the glyceride of hydroxy fatty acid, in the present invention, includes castor oil and the like.

The hydrolysate of a hydroxy fatty acid derivative used in the present invention can be produced by hydrolyzing the aforementioned hydroxy fatty acid derivative. For example, such hydrolysate can be produced by chemical or enzymatic hydrolysis such as processing with a hydrolase such as lipase and the like, alkaline treatment, or high-pressure steam processing, of a glyceride or alkyl ester of hydroxy fatty acid. The hydrolysate of a hydroxy fatty acid derivative includes, but is not limited to, a castor oil hydrolysate and a hydrolysate of ethyl 11-hydroxypalmitate.

The hydroxy fatty acid and the hydroxy fatty acid derivative used in the present invention may be an optically active (R) or (S) form, or a racemic modification. In the present invention, for example, when an optically active hydroxy fatty acid represented by the general formula (2-1):

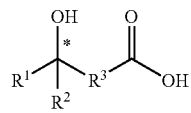

(2-1)

wherein * represents a chiral carbon atom and $R^1$ to $R^3$ are as defined above is used as the hydroxy fatty acid represented by the general formula (2), the resulting a lactone is an optically active lactone. When $R^1$ is identical to $R^2$, a carbon atom to which $R^1$ and $R^2$ are bound is not a chiral carbon atom.

When an optically active hydroxy fatty acid derivative is used as a hydroxy fatty acid derivative, the resulting a lactone is also an optically active lactone.

For example, the optically active lactone can be obtained with the use of the optically active alkyl ester of hydroxy fatty acid represented by the general formula (3-1):

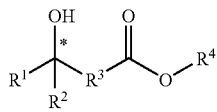

(3-1)

wherein $R^1$ to $R^4$ and * are as defined above, as the alkyl ester of the hydroxy fatty acid represented by the above-mentioned general formula (3) or the optically active glyceride of hydroxy fatty acid represented by the general formula (4-1):

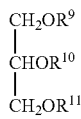

(4-1)

wherein $R^9$ to $R^{11}$ each independently represent a hydrogen atom or a group represented by the general formula (6-1):

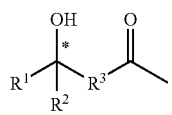

(6-1)

wherein $R^1$ to $R^3$ and * are as defined above, provided that at least one of $R^9$ to $R^{11}$ is a group represented by the general formula (6-1), as the glyceride of hydroxy fatty acid represented by the above-mentioned general formula (4).

The optically active glyceride of an hydroxy fatty acid includes an optically active monoglyceride of hydroxy fatty acid, an optically active diglyceride of hydroxy fatty acid, an optically active triglyceride of hydroxy fatty acid and the like.

Further, when a hydrolysate of a hydroxy fatty acid derivative is used in the present invention, the same is true of the use of an optically active hydroxy fatty acid derivative as a hydroxy fatty acid derivative to be hydrolyzed.

More specifically, if the hydroxy group-binding carbon has R-configuration, the resulting optically active a lactone is an R-lactone. If the hydroxy group-binding carbon has S-configuration, the resulting optically active lactone is an S-lactone.

A preferable example of the optically active hydroxy fatty acid represented by the general formula (2-1) is an optically active form of a hydroxy fatty acid that was presented as the aforementioned preferable example of the hydroxy fatty acid. Optically active ricinoleic acid, optically active 11-hydroxypalmitic acid, optically active lesquerolic acid, optically active 10-hydroxystearic acid, optically active 10-hydroxypalmitic acid and the like are preferable among them.

Preferable examples of the optically active alkyl ester of hydroxy fatty acid represented by the general formula (3-1) include optically active ethyl 11-hydroxypalmitate, optically active ethyl ricinoleate, optically active ethyl lesquerolate, optically active ethyl 10-hydroxystearate, and optically active ethyl 10-hydroxypalmitate and the like.

A preferable example of the optically active glyceride of hydroxy fatty acid represented by the general formula (4-1) includes, for example, optically active castor oil.

In order to produce γ-decalactone as a lactone by the production method of the present invention, at least one member selected from the group consisting of, but is not limited to castor oil a castor oil hydrolysate, ricinoleic acid, and lesquerolic acid is preferably used as a hydroxy fatty acid, a hydroxy fatty acid derivative, or a hydrolysate of a hydroxy fatty acid derivative. When producing δ-decalactone by the production method of the present invention, use of, but are not limited to, 11-hydroxypalmitic acid and/or ethyl 11-hydroxypalmitate, as a hydroxy fatty acid, a hydroxy fatty acid derivative, or a hydrolysate of a hydroxy fatty acid derivative, is preferable.

The hydroxy fatty acid, the hydroxy fatty acid derivative, or the hydrolysate of a hydroxy fatty acid derivative used in the present invention may be a commercial product or may be extracted from natural substances. Alternatively, it may be manufactured as appropriate. In order to obtain a natural lactone by the production method of the present invention, use of a hydroxy fatty acid, a hydroxy fatty acid derivative, or a hydrolysate of a hydroxy fatty acid derivative that was obtained by process other than chemical synthesis is preferable. For example, 11-hydroxypalmitic acid can be preferably extracted from a jalap or sweet potato for the purpose of its use in producing natural δ-decalactone. In order to obtain an optically active lactone by the production method of the present invention as mentioned above, use of an optically active form of a hydroxy fatty acid, a hydroxy fatty acid derivative, or a hydrolysate of a hydroxy fatty acid derivative-is preferable.

A culture medium that is used for producing a lactone in the present invention contains at least one selected from the group consisting of the hydroxy fatty acid, the hydroxy fatty acid derivative, and the hydrolysate of the hydroxy fatty acid derivative mentioned above in amounts of 10% (w/v) to 50% (w/v), and preferably 15% (w/v) to 25% (w/v), per one liter of the medium.

The medium that is used for producing a lactone in the present invention can be prepared by adding other conventional components for cell culture (e.g., a nitrogen source etc.) to at least one selected from the group consisting of the hydroxy fatty acid, the hydroxy fatty acid derivative, and the hydrolysate of the hydroxy fatty acid derivative as mentioned above, if needed. Other components to be added to the medium include, but are not limited to, nitrogen sources such as yeast extract, urea, corn steep liquor, ammonium sulfate, and diammonium hydrogen phosphate; additional carbon sources such as malt extract, polypeptone, and saccharides such as glucose; inorganic salts such as manganese sulfate, calcium chloride, ferric chloride, ferrous sulfate, ferric sulfate, zinc sulfate, copper sulfate, magnesium sulfate, cobalt chloride, sodium molybdate, boron, and potassium iodide; coenzymes such as flavin mononucleotide (FMN), flavin adenine dinucleotide (FAD), nicotinamide adenine dinucleotide (NAD), nicotinamide adenine dinucleotide phosphate (NADP), and coenzyme A (CoA); nucleotides such as adenosine triphosphate (ATP); vitamins such as L-carnitine; and sterilized water. Cofactors such as inorganic salts, coenzymes, and vitamins can further increase the amount of a lactone precursor hydroxy fatty acid and/or a lactone produced, and the amounts thereof to be added may be usually very small. A person skilled in the art can easily determine such other components for preparing a medium in which *Candida sorbophila* can grow, as appropriate.

(3) Production of an Optically Active Lactone Using *Candida sorbophila*

In the present invention, culturing of the *Candida sorbophila* as described in (1) above in the medium for producing a lactone as described in (2) above enables *Candida sorbophila* to produce a lactone precursor hydroxy fatty acid and/or a lactone in the medium.

The lactone precursor hydroxy fatty acid that was produced by *Candida sorbophila* can be converted into a lactone by lactonization thereof. The lactone precursor hydroxy fatty acid can be lactonized by any method known to a person skilled in the art. For example, the lactonization can be carried out by heating treatment under acidic conditions. More specifically, such processing can be carried out by heating a culture containing the lactone precursor hydroxy fatty acid under conditions of pH 3 to 5 and 100° C. for 20 minutes and thereby lactonizing a lactone precursor hydroxy fatty acid in the culture product. The lactonized compound derived from the lactone precursor hydroxy fatty acid is the lactone according to the present invention. In the present invention, lactonization can be carried out without the use of a pH adjustor.

The lactone obtained by lactonization of a lactone precursor hydroxy fatty acid that is produced by the aforementioned process or the lactone produced by *Candida sorbophila* can be recovered and/or isolated and purified by a method known to a person skilled in the art.

The term "lactone precursor hydroxy fatty acid" used herein refers to a hydroxy fatty acid that can be lactonized. The "lactone precursor hydroxy fatty acid" according to the present invention is, preferably, a hydroxy fatty acid which has hydroxy in the 4- or 5-position from the carbon atom of carboxy and has at least 4, preferably 5 to 22, more preferably 5 to 17, and further preferably 5 to 12 carbon atoms.

A specific example of the lactone precursor hydroxy fatty acid includes a hydroxy fatty acid represented by the general formula (5):

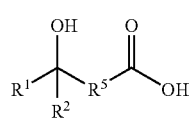

(5)

wherein $R^5$ represents an optionally substituted divalent hydrocarbon group having a 2 or 3-carbon chain; $R^1$ and $R^2$ are as defined above; and alternatively, $R^2$ and $R^5$ may be bonded to form a ring.

$R^5$, an optionally substituted divalent hydrocarbon group, include a divalent hydrocarbon group having a 2 or 3-carbon chain and a divalent substituted hydrocarbon group having a 2 or 3 carbon-chain.

The divalent hydrocarbon group having a 2 or 3-carbon chain includes alkylene having a 2 or 3-carbon chain of ethylene or trimethylene and alkenylene having a 2 or 3-carbon chain of ethenylene or propenylene.

The divalent substituted hydrocarbon group having a 2 or 3-carbon chain is a group derived from the aforementioned divalent hydrocarbon group having a 2 or 3-carbon chain by substitution of at least 1 hydrogen atom with the aforementioned substituent other than hydroxy. A specific example of the divalent substituted hydrocarbon group having a 2 or 3-carbon chain includes propylene and the like. When $R^2$ and $R^5$ are bonded to form a ring, the resulting ring includes an aliphatic ring and an aromatic ring. The aliphatic ring includes a cyclobutane ring, a cyclopentane ring, a cyclohexane ring, a cyclohexene ring and the like. The aromatic ring includes a benzene ring and the like.

Specific examples of the lactone precursor hydroxy fatty acid used in the present invention represented by the general formula (5), wherein $R^5$ represents hydrocarbon having a 2-carbon chain, include γ-hydroxydecanoic acid, a hydroxy fatty acid represented by the following formulae and the like.

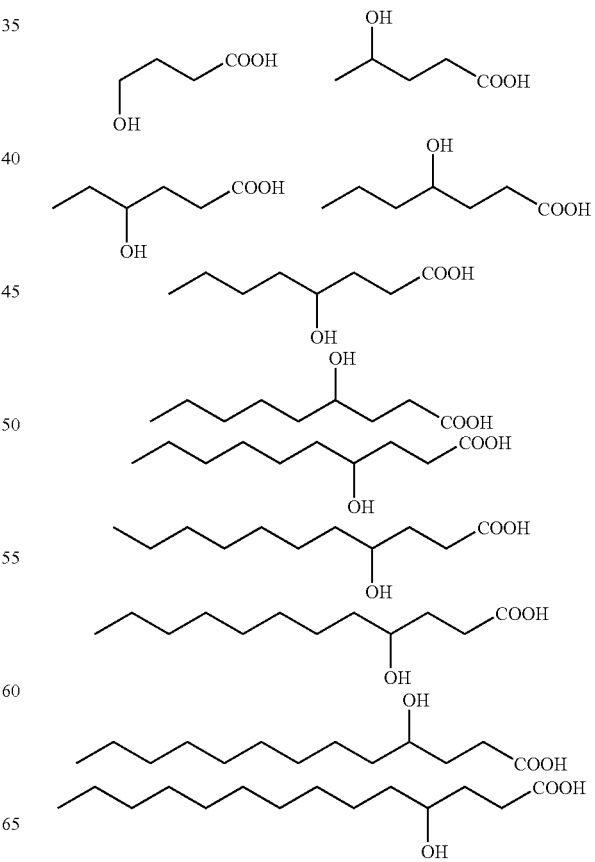

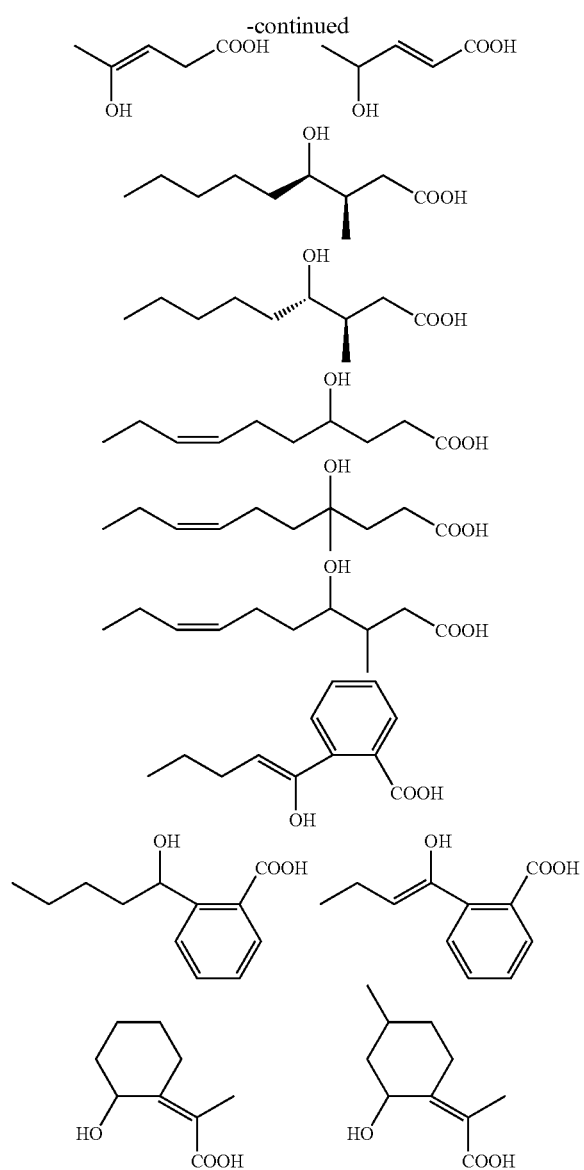

Specific examples of the lactone precursor hydroxy fatty acid represented by the general formula (5), wherein $R^5$ is a hydrocarbon group having a 3 carbon chain, include δ-hydroxydecanoic acid and the hydroxy fatty acid represented by following formulae.

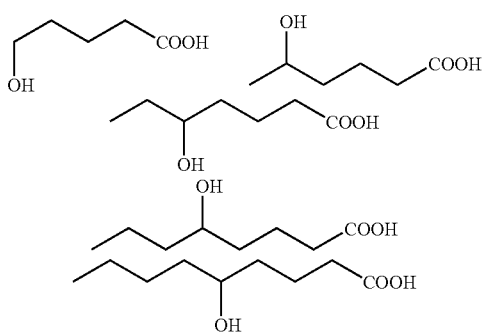

When an optically active substance of a hydroxy fatty acid, of a hydroxy fatty acid derivative, or of a hydrolysate of a hydroxy fatty acid derivative is used in the method of the present invention, the resulting lactone precursor hydroxy fatty acid is the optically active one represented by the general formula (5-1):

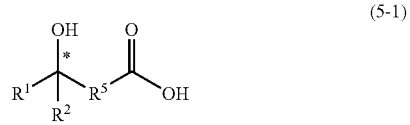

(5-1)

wherein $R^1$, $R^2$, $R^5$, and * are as defined above. In the present invention, an optically active lactone precursor hydroxy fatty acid is preferably used as the lactone precursor hydroxy fatty acid.

The lactone obtained by the production method of the present invention is represented by, for example, the general formula (1):

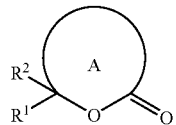
(1)

wherein ring A represents a lactone ring; $R^1$ and $R^2$ are as defined above, in which ring A and $R^2$ may be bonded to form a ring.

The lactone ring represented by ring A in the general formula (1) includes a γ-lactone ring represented by the following formula (7) and a δ-lactone ring represented by the following formula (8). Ring A may also have a substituent.

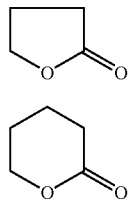

Specific examples of the rings formed together between ring A and $R^2$ include rings represented by the following formulae.

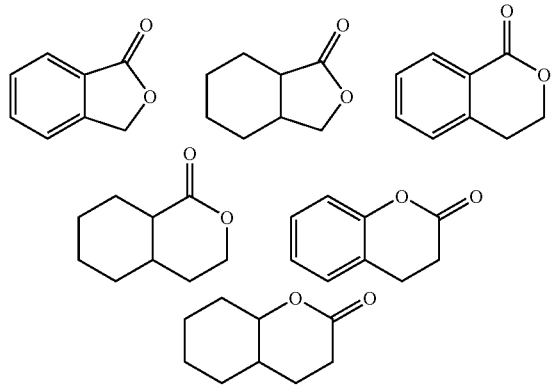

Examples of the a lactone obtained by the production method of the present invention include, but are not limited to, a lactone having 4 or more carbon atoms. Specific examples thereof include γ-decalactone, γ-valerolactone, γ-hexalactone, γ-heptalactone, γ-octalactone, γ-nonalactone, γ-undecalactone, γ-dodecalactone, γ-tridecalactone, γ-tetradecalactone, δ-decalactone, δ-hexalactone, δ-heptalactone, δ-octalactone, δ-nonalactone, δ-undecalactone, δ-dodecalactone, δ-tridecalactone, δ-tetradecalactone, angelica lactone, whisky lactone, γ-jasmolactone, jasmine lactone, lactone of cis-jasmone, methyl γ-decalactone, jasmolactone, menthalactone, n-butyl phthalide, propylidene phthalide, butylidene phthalide, 4,6,6,(4,4,6)-trimethyltetrahydropyran-2-one, δ-2-decenolactone, coumarin, dihydrocoumarin, cyclohexyl lactone, 6-methylcoumarin, and a lactone represented by the following formulae.

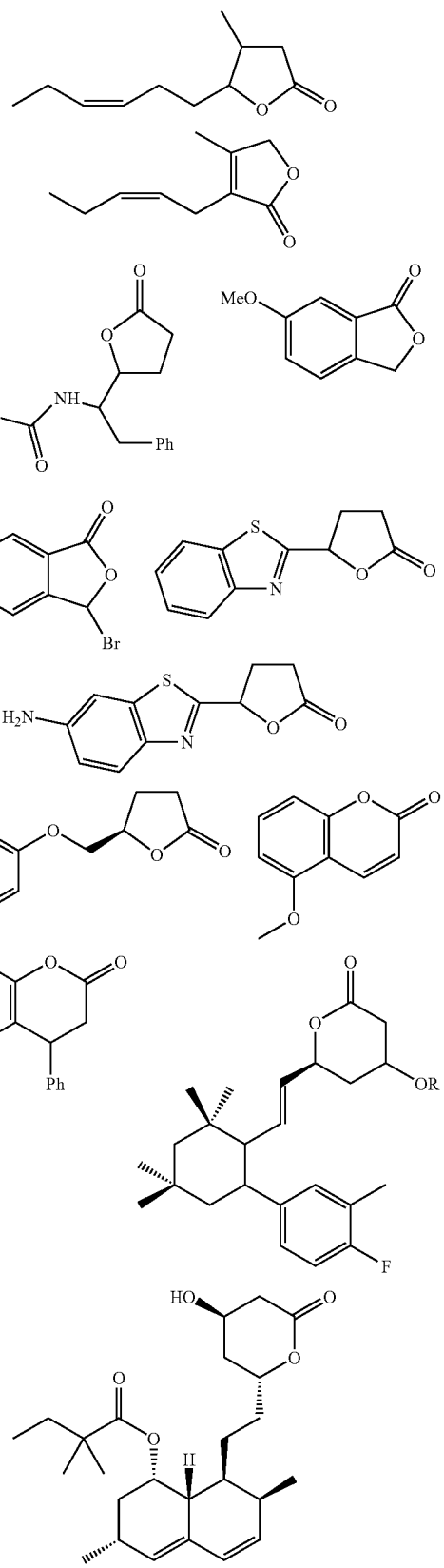

-continued

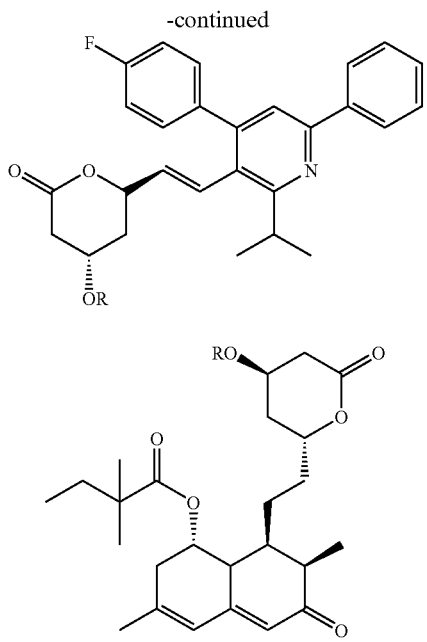

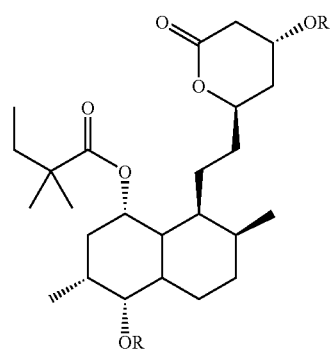

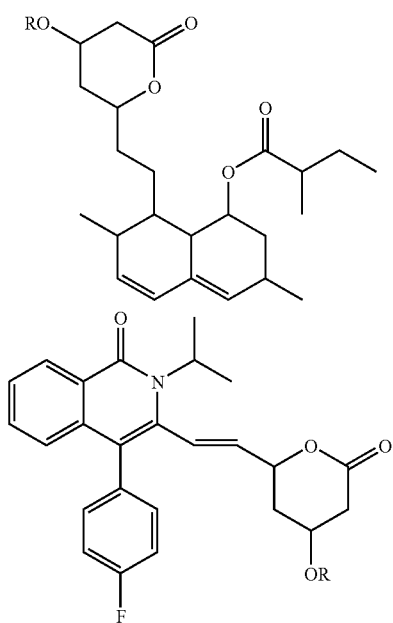

-continued

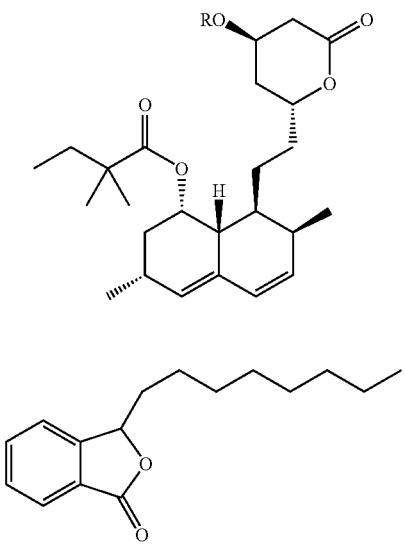

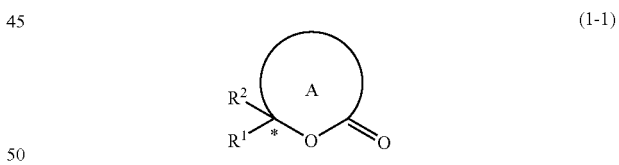

In the above formulae, R represents a protecting group.

Among the aforementioned, a lactone having carbon numbers 5 to 12, such as γ-decalactone, γ-valerolactone, γ-hexalactone, γ-heptalactone, γ-octalactone, γ-nonalactone, γ-undecalactone, γ-dodecalactone, γ-tridecalactone, γ-tetradecalactone, δ-decalactone, δ-heptalactone, δ-hexalactone, δ-octalactone, δ-nonalactone, δ-undecalactone, δ-dodecalactone, δ-tridecalactone, and δ-tetradecalactone, are particularly preferable.

When an optically active form of a hydroxy fatty acid, a hydroxy fatty acid derivative, or a hydrolysate of a hydroxy fatty acid derivative is used in the production method of the present invention, the resulting lactone is an optically active lactone.

An example of the optically active lactone, for example, is represented by general formula (1-1):

(1-1)

wherein ring A, $R^1$, $R^2$, and * are as defined above.

The term "optically active lactone" used herein refers to a lactone that is optically active substance (for example, an R or S form). The optically active lactone produced by the method of the present invention is generated by lactonization of a lactone precursor hydroxy fatty acid that is produced from a hydroxy fatty acid by the use of *Candida sorbophila*. Alternatively, the optically active lactone is produced from a hydroxy fatty acid by the use of *Candida sorbophila*.

The optically active lactone obtained by the production method of the present invention include, but are not limited to, an optically active lactone having at least 5 and preferably 5 to 12 carbon atoms. For example, an optically active form of the lactone presented as a specific example above can be obtained. Preferable examples thereof include an optically active γ-decalactone, an optically active γ-valerolactone, an optically active γ-hexalactone, an optically active γ-heptalactone, an optically active γ-octalactone, an optically active γ-nonalactone, an optically active γ-undecalactone, an optically active γ-dodecalactone, an optically active γ-tridecalactone, an optically active γ-tetradecalactone, an optically active δ-decalactone, an optically active δ-hexalactone, an optically active δ-heptalactone, an optically active δ-octalactone, an optically active δ-nonalactone, an optically active δ-undecalactone, an optically active δ-dodecalactone, an optically active δ-tridecalactone, and an optically active δ-tetradecalactone.

(4) Production of an Optically Active γ-decalactone by the Method of the Present Invention The method for producing an optically active lactone of the present invention is hereafter described in greater detail by employing the production of an optically active γ-decalactone as an example. The method for producing an optically active lactone of the present invention can be basically carried out by procedures that are the same as those for producing an optically active γ-decalactone.

a) Medium Used for Culture for Producing an Optically Active γ-hydroxydecanoic Acid and/or an Optically Active γ-decalactone (Medium for Main Culture)

According to the present invention, at least one selected from the group consisting of castor oil, a castor oil hydrolysate, ricinoleic acid, and lesquerolic acid is used as a carbon source for the medium when culturing for the purpose of producing an optically active γ-hydroxydecanoic acid and/or an optically active γ-decalactone (referred to as the main culture in the Examples). In the present invention, a castor oil hydrolysate refers to a mixture obtained by chemically or enzymatically hydrolyzing castor oil. A castor oil hydrolysate includes a hydrolysate obtained by hydrolyzing castor oil by the use of lipase (hereafter it is referred to as "lipase-treated hydrolysate"). A main component of the hydrolysate obtained by hydrolyzing castor oil by the use of lipase is ricinoleic acid. Accordingly, a castor oil hydrolysate is mainly composed of, for example, ricinoleic acid that is a main fatty acid consisting castor oil.

Any lipase can be used for hydrolyzing castor oil without particular limitations as long as it can produce ricinoleic acid from castor oil. Examples of such lipase, for example, include: Lipase OF and Lipase MY (Meito Sangyo Co., Ltd.); and Newlase F3G, Lipase A "Amano" 6, Lipase AY "Amano" 30G, Lipase F-AP 15, Lipase G "Amano" 50, Lipase M "Amano" 10, and Lipase R "Amano" G (Amano Enzyme Inc.). A lipase-treated hydrolysate can be obtained under conditions where a hydrolysate mainly composed of ricinoleic acid is generated from castor oil, for example, via incubation with the addition of 0.5 g of lipase per 100 g of castor oil at 30° C. for 24 hours. This lipase-treated hydrolysate can be directly used in mixture form.

When a castor oil hydrolysate is contained in the main culture medium according to the present invention, a lipase-treated hydrolysate is preferably added to the medium. In the production method of the present invention, however, inclusion of castor oil in the medium results in the inclusion of a lipase-treated hydrolysate in the medium after the culture due to the following reason. That is, according to the method of the present invention, a hydrolysate is generated from castor oil in a medium with the aid of the *Candida sorbophila* that is used in the present invention. Accordingly, addition of a lipase-treated hydrolysate is an optional step if castor oil is contained in the medium.

In the present invention, at least one selected from the group consisting of castor oil, a castor oil hydrolysate, ricinoleic acid, and lesquerolic acid may be used. These substances may be used alone, or in any combinations of two or more as appropriate. Among them, castor oil and/or a castor oil hydrolysate are particularly preferable.

The concentration of at least one selected from the group consisting of castor oil, a castor oil hydrolysate, ricinoleic acid, and lesquerolic acid to be added to the medium is generally about 10% to 50% (w/v), and preferably about 15% to 25% (w/v) per liter of the medium.

The medium used in the present invention may further contain other components such as yeast extract, malt extract, polypeptone, and glucose, if needed. Such medium containing additional components can be employed as a nutrient medium to produce the γ-hydroxydecanoic acid and/or optically active γ-decalactone of the present invention.

Yeast extract, urea, corn steep liquor, ammonium sulfate, diammonium hydrogen phosphate, and the like can be incorporated into the aforementioned medium as nitrogen sources. Also, malt extract, polypeptone, and saccharides such as glucose and the like can be incorporated into the medium as additional carbon sources.

Alternatively, a synthetic medium containing at least one selected from the group consisting of castor oil, a castor oil hydrolysate, ricinoleic acid, and lesquerolic acid as a single carbon source may also be used. This synthetic medium may further contain additional components such as the additional nitrogen sources or carbon sources mentioned above.

The yield of an optically active γ-hydroxydecanoic acid and/or an optically active γ-decalactone produced can be further increased by optionally adding a variety of cofactors to the aforementioned medium.

Cofactors include: inorganic salts such as manganese sulfate, calcium chloride, ferric chloride, ferrous sulfate, ferric sulfate, zinc sulfate, copper sulfate, magnesium sulfate, cobalt chloride, sodium molybdate, boron, and potassium iodide; coenzymes such as flavin mononucleotide (FMN), flavin adenine dinucleotide (FAD), nicotinamide adenine dinucleotide (NAD), nicotinamide adenine dinucleotide phosphate (NADP), and coenzyme A (CoA); nucleotides such as adenosine triphosphate (ATP); and vitamins such as L-carnitine. The amount of a cofactor to be added may be very small.

The main culture medium used in the present invention includes a medium prepared by adding at least one selected from the group consisting of castor oil, a castor oil hydrolysate, ricinoleic acid, and lesquerolic acid to YM medium, potato dextrose medium, or potato sucrose medium and a medium prepared by adding any of the aforementioned additional components to the medium mentioned above.

b) Production of an Optically Active γ-hydroxydecanoic Acid and/or an Optically Active γ-decalactone by Main Culture In the present invention, γ-hydroxydecanoic acid and/or an optically active γ-decalactone can be produced and accumulated in a medium by culturing the *Candida sorbophila* according to the present invention in the medium described in a) above.

The *Candida sorbophila* according to the present invention may be directly inoculated and cultured on the medium a). However, preferably, such *Candida sorbophila* is previously subjected to seed culture in a conventional medium, and the resultant is then inoculated or spread on the medium a) for culture. Conditions for seed culture may be identical to those for culture (main culture) for producing γ-hydroxydecanoic acid and/or an optically active γ-decalactone. However, the conditions are not particularly limited as long as the *Candida sorbophila* strain can be proliferated. A conventional medium that is used for seed culture may be solid or liquid. It may or may not contain at least one selected from the group consisting of castor oil, a castor oil hydrolysate, ricinoleic acid, and lesquerolic acid. A seed culture medium includes YM slant agar medium and potato dextrose slant agar medium. The amount of the seed culture product to be added to the medium for main culture is not particularly limited. When the seed culture product is, for example, liquid, however, a culture product having an absorbance at 610 nm (OD 610) of approximately 30 is preferably added in amounts of 1% to 3% relative to the amount of the main culture medium. Alternatively, seed culture may be followed by preculture, and main culture may be then carried out in the medium a). Such two-phase culture is suitable for mass-production and is particularly useful for industrial production. Conditions for preculture may be identical to those for main culture. However, the conditions are not particularly limited as long as the *Candida sorbophila* strain can be proliferated. The seed culture medium may or may not contain at least one selected from the group consisting of castor oil, a castor oil hydrolysate, ricinoleic acid, and lesquerolic acid.

In the production method of the present invention, culture conditions are aerobic. Culture temperature is selected as appropriate in the range of generally 20° C. to 35° C., and preferably 24° C. to 30° C. The pH level of the medium is selected as appropriate generally between 5 and 7, and preferably between 5.5 and 6.5. Culture is carried out, for example, in shaking culture in a shake flask or a fermenter (e.g., a fermenter equipped with an agitator and aerator).

The duration of main culture is not particularly limited as long as it is long enough to produce an optically active γ-hydroxydecanoic acid and/or an optically active γ-decalactone. Preferably, the duration is selected in a manner such that the amount of optically active γ-hydroxydecanoic acid and/or optically active γ-decalactone produced reaches the maximal level. Such duration varies depending on, for example, the composition of the medium, the amount of at least one selected from the group consisting of castor oil, a castor oil hydrolysate, ricinoleic acid, and lesquerolic acid to be added as a substrate, and the aeration and agitation efficiency in accordance with the culture apparatus employed. In the case of culture using a shake flask as a culture apparatus, for example, the culture duration may be selected as appropriate in the range of generally 1 hour to 30 days, and preferably 12 hours to 25 days. In the case of culture using a fermenter, the culture duration may be selected as appropriate in the range of generally 1 day to 20 days, and preferably 3 to 10 days. Use of a fermenter can result in the completion of culture within a relatively short period of time and thus is preferable from the viewpoint of production efficiency.

The culture duration that is long enough to bring about the adequate amount of optically active γ-decalactone produced may be determined in the following manner. The optically active γ-decalactone produced in a medium is sampled over the time course. Alternatively, the γ-hydroxydecanoic acid produced in a medium is sampled over the time course and then lactonized. The amount of the resulting optically active γ-decalactone is then determined by gas chromatography (GC), thin-layer chromatography (TLC), or gas chromatography/mass spectrometry (GC-MS) and is further compared with the standard if needed.

c) Production of an Optically Active γ-decalactone From an Optically Active γ-hydroxydecanoic Acid The optically active γ-hydroxydecanoic acid as produced in a medium in the manner described above can be used as a pharmaceutical intermediate or the like in that state. In the present invention, however, the γ-hydroxydecanoic acid is further used to produce an optically active γ-decalactone by conversion of the γ-hydroxydecanoic acid by lactonization.

Lactonization may be carried out by any conventional technique thereof. Lactonization of the optically active γ-hydroxydecanoic acid of the present invention may be carried out after the γ-hydroxydecanoic acid produced in the aforementioned medium is recovered by a conventional technique. Alternatively, it may be carried out while the culture medium contains the optically active γ-hydroxydecanoic acid by direct lactonization of the medium after the completion of culture.

The aforementioned lactonization may be carried out by a conventional technique, such as lactonization in a culture solution. A specific example of such method is one wherein an acid such as dilute hydrochloric acid or dilute sulfuric acid is added to the culture solution after the completion of culture to acidify the culture solution.

In the present invention, lactonization is preferably carried out without acidifying the culture solution in order to obtain an optically active γ-decalactone as a compound having properties as close as possible to those thereof in a natural state. Since the pH level of the culture solution after the completion of culture is already in an acidic range of between 3.0 and 4.5 in the present invention, an acidic culture solution can be obtained without further acidifying the culture solution. Lactonization of the optically active γ-hydroxydecanoic acid contained in the culture solution can be realized for such acidic culture solution by heating it for generally approximately 10 minutes to 1 hour, and preferably approximately 10 to 30 minutes, without acidifying the culture solution. This heating temperature is set at approximately 70° C. to 130° C., and preferably at approximately 90° C. to 120° C. When lactonization is carried out in the present invention, the pH level of the medium within the acidic conditions is sufficient, and it is preferably between pH 2 and 5.

In the present invention, such lactonization of an optically active γ-hydroxydecanoic acid can result in the conversion of the optically active γ-hydroxydecanoic acid into the optically active γ-decalactone.

The obtained optically active γ-decalactone may be recovered and purified from a culture solution by a conventional technique such as solvent extraction and distillation after cells are separated and removed from the culture solution by centrifugation or other means.

According to the method for producing optically active γ-decalactone of the present invention, R-γ-decalactone of high optical purity can be obtained.

The lactone obtained by the production method of the present invention can be used for flavor and fragrance substances, pharmaceutical intermediates, and the like. For example, R-γ-decalactone can be used for adding, strengthening, or enhancing organolepticities for beverages, chewing gum, fruit juice, tobacco products, pharmaceutical preparations, flavor and/or fragrance preparations, scented products, and the like. R-γ-decalactone has an aroma that is stronger than that of S-γ-decalactone and advantageously has a more natural fruit-like aroma as its characteristic (A. Mosandle et al., J. Agric. Food Chem., 37, 413, 1989).

(5) Conclusion

The production method of the present invention is characterized by use of *Candida sorbophila*. According to the method of the present invention, an optically active lactone such as R-γ-decalactone or R-δ-decalactone can be obtained with high optical purity. Also, the method for producing optically active γ-decalactone of the present invention has the high efficiency in terms of producing R-γ-decalactone. Such high production efficiency provided by the method of the present invention is probably due to the fact that presence of *Candida sorbophila* less leads to destroy the generated R-γ-decalactone in the production system of the present invention. Particularly, it is presumed that *Candida sorbophila* does not decompose R-γ-decalactone, resulting in the high production efficiency. However, it is noted that the technical scope of the present invention should not be limited based on such hypothetical theory.

The method of the present invention facilitates the effective production of an optically active lactone of high purity and can improve the working efficiency in industrial production.

PREFERRED EMBODIMENTS OF THE INVENTION

The present invention is hereafter described in more detail with reference to the examples, although the technical scope of the present invention is not limited thereto.

In the following examples, gas chromatography (GC) analysis was carried out under the following conditions.
Apparatus: Model: 5890, Hewlett Packard
Column: BC-WAX (0.25 mm (diameter)×30 m (length), GL Sciences)
Internal standard sample: ethyl decanoate (1.0 v/v%)

The optical purities of the lactones produced in the Examples were assayed via GC analysis (apparatus: G3000, column: Chirasil-DEX-CB, 0.25 mm (diameter)×25 m (length), Hitachi).

EXAMPLE 1

The FC 58 strain was inoculated on YM slant agar medium and cultured at 27° C. for 3 days for activation. A medium for preculture was prepared in the following manner. At the outset, 0.09 g of yeast extract, 0.09 g of malt extract, 0.15 g of polypeptone, and 0.3 g of glucose were placed in a 300-mL volume Erlenmeyer flask, distilled water was added thereto to bring the total volume to 30 mL, pH 6. The resultant was sterilized in an autoclave at 121° C. for 15 minutes. The thus prepared medium was cooled, the FC 58 strain activated in the manner described above was inoculated thereon, and shaking culture was carried out in a rotary shake culture apparatus at 27° C. and 150 rpm for 24 hours for preparation of a preculture solution. Further, a medium for the subsequent main culture was prepared. Specifically, 0.3 g of yeast extract, 0.3 g of malt extract, and 0.5 g of polypeptone were placed in a 500-mL volume Sakaguchi flask, distilled water was added thereto to bring the total volume to 100 ml. pH 6. and 20 g of castor oil was further added thereto. The resultant was sterilized in an autoclave at 121° C. for 15 minutes. Subsequently, the medium for main culture was cooled, 2 ml of the aforementioned preculture solution was inoculated thereon, and main culture was carried out via shaking culture at 27° C. and 150 rpm. The pH level was not adjusted during the culture. After the culture, the pH level of the culture solution was 4.06. Aseptic sampling of the culture solution in volumes of 5 ml each was initiated 3 days after the initiation of culture, sampling was conducted over the time course, and the sampled culture solutions (the samples) were independently heated to 100° C. for 20 minutes to lactonize γ-hydroxydecanoic acid. After such lactonization, the sample was subjected to extraction with ethyl acetate, and the separated organic layer was quantified via gas chromatography (GC) analysis by the internal standard method (with the use of ethyl decanoate as the internal standard sample). As a result, the amount of R-γ-decalactone produced in the culture solution was found to become maximal 14 days after the initiation of culture. Such amount of R-γ-decalactone was 8.41 g per liter of the main culture medium. The optical purity thereof was 99% ee or higher.

EXAMPLE 2

R-γ-decalactone was produced in the same manner as in Example 1 except for the use of 20 g of ricinoleic acid (purity of 80% or higher, Wako Pure Chemical Industries, Ltd.) instead of 20 g of castor oil. As a result, the amount of R-γ-decalactone produced in the culture solution was found to become maximal 20 days after the initiation of culture. Such amount of R-γ-decalactone was 21.89 g per liter of the main culture medium. The optical purity thereof was 99% ee or higher.

EXAMPLE 3

R-γ-decalactone was produced in the same manner as in Example 2 except for the addition of 1.7 mg of manganese sulfate ($MnSO_4.H_2O$), 0.55 mg of calcium chloride ($CaCl_2.H_2O$), 0.375 mg of ferric chloride ($FeCl_3.H_2O$), 2.2 mg of zinc sulfate ($ZnSO_4.H_2O$), 0.4 mg of copper sulfate ($CuSO_4.H_2O$), 5.9 mg of magnesium sulfate ($MgSO_4.H_2O$), 0.28 mg of cobalt chloride ($CoCl_2.H_2O$), 0.26 mg of sodium molybdate ($Na_2MoO_4.H_2O$), 0.4 mg of boron ($H_3BO_3$), and 0.06 mg of potassium iodide (KI) to the main culture medium. As a result, the amount of R-γ-decalactone produced in the culture solution was found to become maximal 20 days after the initiation of culture. Such amount of R-γ-decalactone was 27.37 g per liter of the main culture medium. The optical purity thereof was 99% ee or higher.

EXAMPLE 4

The FC 58 strain was inoculated on YM slant agar medium and cultured at 27° C. for 3 days for activation. A medium for preculture was prepared in the following manner. At the outset, 0.3 g of yeast extract, 0.3 g of malt extract, 0.5 g of polypeptone, and 1.0 g of glucose were placed in a 500-mL volume Sakaguchi flask, distilled water was added thereto to bring the total volume to 100 ml, pH 6. The resultant was sterilized in an autoclave at 121° C. for 15 minutes. The thus-prepared medium was cooled, the FC 58 strain activated in the manner described above was inoculated thereon, and shaking culture was carried out in a rotary shake culture apparatus at 27° C. and 150 rpm for 24 hours for preparation of a preculture solution. Further, a medium for the subsequent main culture was prepared. Specifically, 6.0 g of yeast extract, 6.0 g of malt extract, 10.0 g of polypeptone, 34 mg of manganese sulfate ($MnSO_4.H_2O$), 11 mg of calcium chloride ($CaCl_2.H_2O$), 7.5 mg of ferric chloride ($FeCl_3.H_2O$), 44 mg of zinc sulfate ($ZnSO_4.H_2O$), 8.0 mg of copper sulfate ($CuSO_4.H_2O$), 118 mg of magnesium sulfate ($MgSO_4.H_2O$), 5.6 mg of cobalt chloride ($CoCl_2.H_2O$), 5.2 mg of sodium molybdate ($Na_2MoO_4 \cdot H_2O$), 8.0 mg of boron ($H_3BO_3$), and 1.2 mg of potassium iodide (KI) were placed in a 5-L volume jar fermenter, distilled water was added thereto to bring the total volume to 2,000 ml, pH 6; and 400 g of ricinoleic acid (purity of 80% or higher, Wako Pure Chemical Industries, Ltd.) was further added thereto. The resultant was sterilized in an autoclave at 121° C. for 15 minutes. Subsequently, the medium for main culture was cooled, 40 ml of the aforementioned preculture solution was inoculated thereon and main culture was carried out under conditions of the agitation rate of 600 rpm, the aeration rate of 1000 ml/mm, and 27° C. The pH level was not adjusted during the culture. After the culture, the pH level of the culture solution was 4.75. Aseptic sampling of the culture solution in volumes of 5 ml each was initiated 3 days after the initiation of culture, sampling was conducted over the time course, and the sampled culture solutions (the samples) were independently heated to 100° C. for 20 minutes to lactonize γ-hydroxydecanoic acid. After such lactonization, the sample was subjected to extraction with ethyl acetate, and the separated organic layer was quantified by GC analysis by the internal standard method (with the use of ethyl decanoate as the internal standard sample). As a result, the amount of R-γ-decalactone produced in the culture solution was found to become maximal 10 days after the initiation of culture. Such amount of R-γ-decalactone was 49.94 g per liter of the main culture medium. The optical purity thereof was 99% ee or higher.

EXAMPLE 5

R-γ-decalactone was produced in the same manner as in Example 4 except for the use of a hydrolysate-obtained by treating 600 g of castor oil with lipase (Lipase OF, Meito Sangyo Co., Ltd.) instead of 400 g of ricinoleic acid (purity of 80% or higher, Wako Pure Chemical Industries, Ltd.). As a result, the amount of R-γ-decalactone produced in the culture solution was found to become maximal 5 days after the initiation of culture. Such amount of R-γ-decalactone was 40.50 g per liter of the main culture medium. The optical purity thereof was 99% ee or higher.

EXAMPLE 6

Optically active γ-decalactone was produced in the same manner as in Example 2 except for the use of the *Candida sorbophila* strain ATCC 74362, the *Candida sorbophila* strain ATCC 60130, or the *Candida sorbophila* strain IFO 1583 instead of the *Candida sorbophila* strain FC 58. As a result, the amounts of γ-decalactone produced in the culture solutions resulting from each of the aforementioned cell strains were found to become maximal 19, 11, and 11 days after the initiation of culture respectively. Such amounts of the γ-decalactone were 13.75 g, 12.97 g, and 12.97 g per liter of the main culture medium, respectively.

EXAMPLE 7

R-γ-decalactone was produced in-the same manner as in Example 1, except that the sampled culture solutions (samples) were not subjected to lactonization via heating. As a result, the amount of R-γ-decalactone produced in the culture solution was found to become maximal 14 days after the initiation of culture. Such amount of R-γ-decalactone was 8.41 g per liter of the main culture medium. The optical purity thereof was 99% ee or higher.

EXAMPLE 8

R-γ-decalactone was produced in the same manner as in Example 2, except that the sampled culture solutions (samples) were not subjected to lactonization via heating. As a result, the amount of R-γ-decalactone produced in the culture solution was found to become maximal 20 days after the initiation of culture. Such amount of R-γ-decalactone was 21.89 g per liter of the main culture medium. The optical purity thereof was 99% ee or higher.

EXAMPLE 9

R-γ-decalactone was produced in the same manner as in Example 3, except that the sampled culture solutions (samples) were not subjected to lactonization via heating. As a result, the amount of R-γ-decalactone produced in the culture solution was found to become maximal 20 days after the initiation of culture. Such amount of R-γ-decalactone was 27.37 g per liter of the main culture medium. The optical purity thereof was 99% ee or higher.

EXAMPLE 10

R-γ-decalactone was produced in the same manner as in Example 4. except that the sampled culture solutions (samples) were not subjected to lactonization via heating. As a result, the amount of R-γ-decalactone produced in the culture solution was found to become maximal 10 days after the initiation of culture. Such amount of R-γ-decalactone was 49.94 g per liter of the main culture medium. The optical purity thereof was 99% ee or higher.

EXAMPLE 11

R-γ-decalactone was produced in the same manner as in Example 5, except that the sampled culture solutions (samples) were not subjected to lactonization via heating. As, a result, the amount of R-γ-decalactone produced in the culture solution was found to become maximal 5 days after the initiation of culture. Such amount of R-γ-decalactone was 40.50 g per liter of the main culture medium. The optical purity thereof was 99% ee or higher.

EXAMPLE 12

R-γ-decalactone was produced in the same manner as in Example 6, except that the sampled culture solutions (samples) were not subjected to lactonization via heating. As a result, the amounts of R-γ-decalactone produced in the culture solutions resulting from each of the aforementioned cell strains were found to become maximal 19, 11, and 11 days after the initiation of culture, respectively. Such amounts of R-γ-decalactone were 13.75 g, 12.97 g, and 12.97 g per liter of the main culture medium, respectively.

EXAMPLE 13

The FC 58 strain was inoculated on YM slant agar medium-and cultured at 27° C. for 3 days for activation. A medium for preculture was prepared in the following manner. At the outset, 0.09 g of yeast extract, 0.09 g of malt extract, 0.15 g of polypeptone, and 0.3 g of glucose were placed in a 300-ml volume Erlenmeyer flask, distilled water was added thereto to bring the total volume to 30 ml, pH 6. The resultant was sterilized in an autoclave at 121° C. for 15 minutes. The thus prepared medium was cooled the FC 58 strain activated in the manner described above was inoculated thereon, and shaking culture was carried out in a rotary shake culture apparatus at 27° C. and 150 rpm for 24 hours for preparation of a preculture solution.

Further, a medium for the subsequent main culture was prepared. Specifically, 0.09 g of yeast extract, 0.09 g of malt extract, 0.15 g of polypeptone, 0.51 mg of manganese sulfate ($MnSO_4.H_2O$), 0.17 mg of calcium chloride ($CaCl_2.H_2O$), 0.11 mg of ferric chloride ($FeCl_3.H_2O$), 0.66 mg of zinc sulfate ($ZnSO_4.H_2O$), 0.12 mg of copper sulfate ($CuSO_4.H_2O$), 1.77 mg of magnesium sulfate ($MgSO_4.H_2O$), 0.08 mg of cobalt chloride ($CoCl_2.H_2O$), 0.08 mg of sodium molybdate ($Na_2MoO_4.H_2O$), 0.12 mg of boron ($H_3BO_3$), and 0.02 mg of potassium iodide (KI) were placed in a 300-mL volume Sakaguchi flask, distilled water was added thereto to bring the total volume to 30 ml, pH 6, and 0.13 g of 11-hydroxy palmitic acid ethyl ester was further added thereto. The resultant was sterilized in an autoclave at 121° C. for 15 minutes. Subsequently, the medium for main culture was cooled, 2 ml of the aforementioned preculture solution was inoculated thereon, and main culture was carried out in shaking culture at 27° C. and 150 rpm. The pH level was not adjusted during the culture. Aseptic sampling of the culture solution in volumes of 5 ml each was initiated 3 days after the initiation of culture, sampling was conducted over the time course, and the sampled culture solutions (the samples) were independently heated to 100° C. for 20 minutes to lactonize δ-hydroxydecanoic acid. After such lactonization, the sample was subjected to extraction with ethyl acetate, and the separated organic layer was quantified by GC analysis by the internal standard method (with the use of ethyl decanoate as the internal standard sample).

As a result, the amount of S-δ-decalactone produced in the culture solution was found to become maximal 11 days after the initiation of culture. Such amount of S-δ-decalactone was 0.019 g per 30 ml of the main culture medium. The optical purity thereof was 96% ee or higher.

EXAMPLE 14

S-δ-decalactone was produced in the same manner as in Example 13, except that the sampled culture solutions (samples) were not subjected to lactonization via heating. As a result, the amount of S-δ-decalactone produced in the culture solution was found to become maximal 11 days after the initiation of culture. Such amount of S-δ-decalactone was 0.019 g per 30 ml of the main culture medium. The optical purity thereof was 96% ee or higher.

REFERENCE EXAMPLE 1

γ-decalactone was produced in the same manner as in Example 2 except for the use of the *Yarrowia lipolytica* strain IFO 0717 known to have high ability of γ-decalactone production instead of the FC 58 strain. As a result, the amount of γ-decalactone produced in the culture solution was found to become maximal 6 days after the initiation of culture. Such amount of γ-decalactone was 4.90 g per liter of the main culture medium. Thereafter, the amount of γ-decalactone produced was monitored over the time course. This revealed that the amount of γ-decalactone produced per liter of the main culture medium began to decrease 6 days after the initiation of culture. The amount of γ-decalactone produced was 3.17 g per liter of the main culture medium 23 days after the initiation of culture.

All publications, patents, and patent applications cited herein are incorporated herein by reference in their entirety.

Industrial Applicability

According to the present invention, a lactone, such as an optically active lactone including an optically active γ-decalactone (e.g., R-γ-decalactone) and an optically active δ-decalactone, can be easily obtained with high production efficiency. Also, a lactone precursor hydroxy fatty acid, such as γ-hydroxydecanoic acid or δ-hydroxydecanoic acid, can be efficiently produced in an intermediary step while the production method of the present invention is carried out. In the production method of the present invention, the addition of an emulsifier or pH adjuster to a medium is not required, and carbon sources, for example, a hydroxy fatty acid, a hydroxy fatty acid derivative, and/or a-hydrolysate of a hydroxy fatty acid derivative, can be added to the medium at concentrations that are high enough for large-scale production. Thus, the method of the present invention is very useful in industrial production.

What is claimed is:

1. A method for producing a lactone comprising culturing *Candida sorbophila* in a medium containing at least one selected from a hydroxy fatty acid, a hydroxy fatty acid derivative, and a hydrolysate of a hydroxy fatty acid derivative, and recovering the produced lactone from the medium.

2. A method for producing a lactone comprising culturing *Candida sorbophila* in a medium containing at least one selected from the group consisting of a hydroxy fatty acid derivative, and a hydrolysate of a hydroxy fatty acid derivative, and lactonizing a lactone precursor hydroxy fatty acid produced in the medium.

3. The method according to claim 1 or 2, wherein the *Candida sorbophila* is at least one selected from *Candida sorbophila* strain ATCC 74362, *Candida sorbophila* strain ATCC 60130, the *Candida sorbophila* strain IFO 1583, and the *Candida sorbophila* strain FC 58 deposited under the accession number FERM BP-8388.

4. The method according to claim 1 or 2, wherein the lactone is represented by general formula (1):

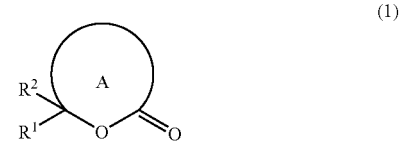

(1)

wherein ring A represents a lactone ring; $R^1$ represents a hydrogen atom, a hydrocarbon group, a substituted hydrocarbon group, a heterocyclic group, or a substituted heterocyclic group; and $R^2$ represents a hydrogen atom, a hydrocarbon group, or a substituted hydrocarbon group; in which ring A and $R^2$ may be bonded to form a ring.

5. The method according to claim 1 or 2, wherein the lactone is an optically active lactone.

6. The method according to claim 1 or 2, wherein the hydroxy fatty acid is represented by general formula (2):

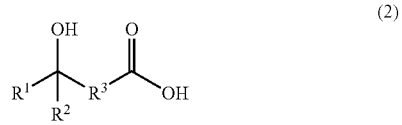

(2)

wherein $R^1$ represents a hydrogen atom, a hydrocarbon group, a substituted hydrocarbon group, a heterocyclic group, or a substituted heterocyclic group; $R^2$ represents a hydrogen atom, a hydrocarbon group, or a substituted hydrocarbon group; and $R^3$ represents an optionally substituted divalent hydrocarbon group having a 4 or more-carbon chain; in which $R^2$ and $R^3$ may be bonded to form a ring.

7. The method according to claim 1 or 2, wherein the hydroxy fatty acid derivative is an alkyl ester of hydroxy fatty acid or a glyceride of hydroxy fatty acid.

8. The method according to claim 7, wherein the alkyl ester of hydroxy fatty acid is represented by general formula (3):

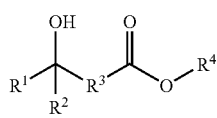

(3)

wherein $R^1$ represents a hydrogen atom, a hydrocarbon group, a substituted hydrocarbon group, a heterocyclic group, or a substituted heterocyclic group; $R^2$ represents a hydrogen atom, a hydrocarbon group, or a substituted hydrocarbon group; $R^3$ represents an optionally substituted divalent hydrocarbon group having a 4 or more-carbon chain; and $R^4$ represents an alkyl group; in which $R^2$ and $R^3$ may be bonded to form a ring.

9. The method according to claim 7, wherein the glyceride of hydroxy fatty acid is represented by general formula (4):

(4)

wherein $R^6$ to $R^8$ each independently represents a hydrogen atom or a group represented by general formula (6):

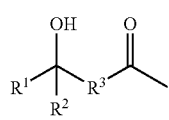

(6)

wherein $R^1$ represents a hydrogen atom, a hydrocarbon group, a substituted hydrocarbon group, a heterocyclic group, or a substituted heterocyclic group; $R^2$ represents a hydrogen atom, a hydrocarbon group, or a substituted hydrocarbon group; $R^3$ represents an optionally substituted divalent hydrocarbon group having a 4 or more-carbon chain; and $R^4$ represents an alkyl group; in which $R^2$ and $R^3$ may be bonded to form a ring, provided that at least one of $R^6$ to $R^8$ is a group represented by the above general formula (6).

10. The method according to claim 1 or 2, wherein *Candida sorbophila* is cultured in a medium containing at least one selected from the group consisting of castor oil, a castor oil hydrolysate, ricinoleic acid, 11-hydroxypalmitic acid, lesquerolic acid, 10-hydroxystearic acid, 10-hydroxypalmitic acid, and ethyl 11-hydroxypalmitate.

11. The method according to claim 2, wherein the lactone precursor hydroxy fatty acid is a hydroxy fatty acid of 4 or more carbon atoms having a hydroxy group at position 4 or 5 thereof.

12. The method according to claim 1 or 2, wherein the lactone is any one selected from the group consisting of γ-decalactone, γ-valerolactone, γ-hexalactone, γ-heptalactone, γ-octalactone, γ-nonalactone, γ-undecalactone, γ-dodecalactone, γ-tridecalactone, γ-tetradecalactone, δ-decalactone, δ-hexalactone, δ-heptalactone, δ-octalactone, δ-nonalactone, δ-undecalactone, δ-dodecalactone, δ-tridecalactone, and δ-tetradecalactone.

13. A method for producing γ-dodecalactone precursor hydroxy fatty acid comprising culturing *Candida sorbophila* in a medium containing at least one selected from castor oil, a castor oil hydrolysate, ricinoleic acid, and lesquerolic acid, and recovering the produced γ-decalactone from the medium.

14. A method for producing γ-decalactone comprising culturing *Candida sorbophila* in a medium containing at least one selected from castor oil, a castor oil hydrolysate, ricinoleic acid, and lesquerolic acid, and recovering the produced γ-decalactone from the medium.

15. The method according to claim 13 or 14, wherein γ-decalactone is an optically active γ-decalactone.

16. The method according to claim 13 or 14, wherein at least one is castor oil and/or a castor oil hydrolysate.

17. A method for producing δ-decalactone comprising culturing *Candida sorbophila* in a medium containing 11-hydroxypalmitic acid and/or ethyl 11-hydroxypalmitate and recovering the produced δ-decalactone from the medium.

18. A method for producing δ-decalactone comprising culturing *Candida sorbophila* in a medium containing 11-hydroxypalmitic acid and/or ethyl 11-hydroxypalmitate and lactonizing δ-hydroxydecanoic acid produced in the medium.

19. The method according to claim 17 or 18, wherein δ-decalactone is an optically active δ-decalactone.

20. The method according to claim 13, 14, 17, or 18, wherein the *Candida sorbophila* is at least one selected from the group consisting of the *Candida sorbophila* strain ATCC 74362, *Candida sorbophila* strain ATCC 60130, the *Candida sorbophila* strain IFO 1583, and the *Candida sorbophila* strain FC 58 deposited under the accession number FERM BP-8388.

* * * * *

UNITED STATES PATENT AND TRADEMARK OFFICE
CERTIFICATE OF CORRECTION

| | |
|---|---|
| PATENT NO. | : 7,129,067 B2 |
| APPLICATION NO. | : 10/519212 |
| DATED | : October 31, 2006 |
| INVENTOR(S) | : Katsuhisa Mitsuhashi and Makoto Iimori |

It is certified that error appears in the above-identified patent and that said Letters Patent is hereby corrected as shown below:

In claim 2, column 36, line 27, "from the group consisting of a" should read --from a hydroxy fatty acid, a--.

In claim 3, column 36, line 34, "60130, the Candida" should read --60130, Candida--.

In claim 3, column 36, lines 34-35, "and the Candida" should read --and Candida--.

In claim 10, column 38, line 5, "from the group consisting of castor" should read --from castor--.

In claim 12, column 38, lines 14-15, "from the group consisting of γ-decalactone," should read --from γ-decalactone,--.

In claim 13, column 38, lines 21-22, "γ-dodecalactone precursor hydroxy fatty acid comprising" should read --γ-decalactone comprising--.

In claim 14, column 38, lines 30-31, "and recovering the produced γ-decalactone from the" should read --and lactonizing γ-hydroxydecanoic acid produced in the--.

In claim 16, column 38, line 34, "wherein at" should read --wherein the at--.

In claim 20, column 38, lines 49-50, "from the group consisting of the Candida" should read --from Candida--.

In claim 20, column 38, lines 51-52, "60130, the Candida" should read --60130, Candida--.

UNITED STATES PATENT AND TRADEMARK OFFICE
CERTIFICATE OF CORRECTION

PATENT NO. : 7,129,067 B2
APPLICATION NO. : 10/519212
DATED : October 31, 2006
INVENTOR(S) : Katsuhisa Mitsuhashi and Makoto Iimori It is certified that error appears in the above-identified patent and that said Letters Patent is hereby corrected as shown below:

In claim 20, column 38, line 52, "and the Candida" should read --and Candida--.

Signed and Sealed this

Sixteenth Day of January, 2007

JON W. DUDAS
*Director of the United States Patent and Trademark Office*